(12) United States Patent
von Oepen et al.

(10) Patent No.: US 11,724,068 B2
(45) Date of Patent: Aug. 15, 2023

(54) INTRAVASCULAR DELIVERY SYSTEM

(71) Applicant: Cephea Valve Technologies, Inc., Santa Clara, CA (US)

(72) Inventors: Randolf von Oepen, Aptos, CA (US); Francisco Valencia, East Palo Alto, CA (US); Sean A. McNiven, Menlo Park, CA (US); Timothy C. Reynolds, Sunnyvale, CA (US); Rommel Cababaro Lumauig, San Jose, CA (US); Shengmin Mei, Fremont, CA (US); Hugo A. Cobar, Sunnyvale, CA (US); Daniel Tucker Wallace, San Jose, CA (US)

(73) Assignee: CEPHEA VALVE TECHNOLOGIES, INC., Santa Clara, CA (US)

( * ) Notice: Subject to any disclaimer, the term of this patent is extended or adjusted under 35 U.S.C. 154(b) by 780 days.

(21) Appl. No.: 16/683,483

(22) Filed: Nov. 14, 2019

(65) Prior Publication Data
US 2020/0155804 A1    May 21, 2020

Related U.S. Application Data

(60) Provisional application No. 62/768,446, filed on Nov. 16, 2018.

(51) Int. Cl.
*A61M 25/01*    (2006.01)
*A61M 25/02*    (2006.01)
*A61M 25/09*    (2006.01)

(52) U.S. Cl.
CPC .... *A61M 25/0136* (2013.01); *A61M 25/0138* (2013.01); *A61M 2025/0286* (2013.01);
(Continued)

(58) Field of Classification Search
CPC .... A61M 25/0136; A61M 2025/09116; A61M 2025/0004; A61F 2/9517; A61F 2/2436
See application file for complete search history.

(56) References Cited

U.S. PATENT DOCUMENTS

| 4,406,656 A | 9/1983 | Hattler et al. |
| 4,432,437 A | 2/1984 | McClung |

(Continued)

FOREIGN PATENT DOCUMENTS

| CN | 1469724 | 1/2004 |
| CN | 1688352 A | 10/2005 |

(Continued)

OTHER PUBLICATIONS

Hironobu Takizawa et al. "Development of a Microfine Active Bending Catheter Equipped with MIF Tactile Sensors", Micro Electro Mechanical Systems, IEEE, Jan. 17, 1999, pp. 412-417.

(Continued)

*Primary Examiner* — Theodore J Stigell
*Assistant Examiner* — Rachel T. Smith
(74) *Attorney, Agent, or Firm* — Workman Nydegger

(57) ABSTRACT

The present disclosure describes devices, systems, and methods for intravascularly delivering an implantable device to a targeted anatomical site such as the mitral annulus. A delivery system includes a delivery member coupled to a handle assembly and extending distally from the handle assembly. A delivery catheter is concentrically positioned within an outer member and configured to advance the intravascular device relative to the outer member. The delivery catheter includes a distal can structure configured to house at least a portion of the intravascular device in a compressed, pre-deployed position.

19 Claims, 17 Drawing Sheets

(52) U.S. Cl.
CPC ............. *A61M 2025/09116* (2013.01); *A61M 2025/09141* (2013.01)

(56) References Cited

U.S. PATENT DOCUMENTS

| | | | |
|---|---|---|---|
| 4,728,319 | A | 3/1988 | Masch |
| 5,053,043 | A | 10/1991 | Gottesman et al. |
| 5,059,213 | A | 10/1991 | Chesterfield et al. |
| 5,078,722 | A | 1/1992 | Stevens |
| 5,078,723 | A | 1/1992 | Dance et al. |
| 5,236,450 | A | 8/1993 | Scott |
| 5,325,845 | A | 7/1994 | Adair |
| 5,345,945 | A | 9/1994 | Hodgson et al. |
| 5,387,219 | A | 2/1995 | Rappe |
| 5,415,664 | A | 5/1995 | Pinchuk |
| 5,472,423 | A | 12/1995 | Gronauer |
| 5,571,085 | A | 11/1996 | Accisano, III |
| 5,662,606 | A | 9/1997 | Cimino et al. |
| 5,669,919 | A | 9/1997 | Sanders et al. |
| 5,769,812 | A | 6/1998 | Stevens et al. |
| 5,807,405 | A | 9/1998 | Vanney et al. |
| 5,820,591 | A | 10/1998 | Thompson et al. |
| 5,843,103 | A | 12/1998 | Wulfman |
| 5,855,601 | A | 1/1999 | Bessler et al. |
| 5,873,882 | A | 2/1999 | Straub et al. |
| 5,902,334 | A | 5/1999 | Dwyer et al. |
| 5,906,642 | A | 5/1999 | Caudillo et al. |
| 5,957,973 | A | 9/1999 | Quiachon et al. |
| 6,090,118 | A | 7/2000 | McGuckin, Jr. |
| 6,180,059 | B1 | 1/2001 | Divino, Jr. et al. |
| 6,228,110 | B1 | 5/2001 | Munsinger |
| 6,458,137 | B1 | 10/2002 | Klint |
| 6,517,550 | B1 | 2/2003 | Konya et al. |
| 6,695,836 | B1 | 2/2004 | DeMello et al. |
| 6,926,725 | B2 | 8/2005 | Cooke et al. |
| 7,172,617 | B2 | 2/2007 | Colgan et al. |
| 7,344,553 | B2 | 3/2008 | Opolski et al. |
| 7,666,204 | B2 | 2/2010 | Thornton et al. |
| 7,736,388 | B2 | 6/2010 | Goldfarb et al. |
| 7,837,727 | B2 | 11/2010 | Goetz et al. |
| 7,988,724 | B2 | 8/2011 | Salahieh et al. |
| 7,993,303 | B2 | 8/2011 | Von Oepen et al. |
| 8,157,852 | B2 | 4/2012 | Bloom et al. |
| 8,523,881 | B2 | 9/2013 | Cabiri et al. |
| 8,647,323 | B2 | 2/2014 | Guo et al. |
| 8,911,455 | B2 | 12/2014 | Quadri et al. |
| 8,926,588 | B2 | 1/2015 | Berthiaume et al. |
| 8,926,692 | B2 | 1/2015 | Dwork |
| 9,339,378 | B2 | 5/2016 | Quadri et al. |
| 9,370,423 | B2 | 6/2016 | Ryan |
| 9,393,112 | B2 | 7/2016 | Tuval et al. |
| 9,399,112 | B2 | 7/2016 | Shevgoor et al. |
| 9,668,859 | B2 | 6/2017 | Kheradvar et al. |
| 9,687,373 | B2 | 6/2017 | Vad |
| 9,693,862 | B2 | 7/2017 | Campbell et al. |
| 9,801,745 | B2 | 10/2017 | Wubbeling et al. |
| 10,111,671 | B2 | 10/2018 | Bodewadt |
| 10,117,760 | B2 | 11/2018 | Mangiardi |
| 10,376,673 | B2 | 8/2019 | Van Hoven et al. |
| 10,398,553 | B2 | 9/2019 | Kizuka |
| 10,470,902 | B2 | 11/2019 | Sheldon et al. |
| 10,646,689 | B2 | 5/2020 | von Oepen et al. |
| 2001/0002445 | A1 | 5/2001 | Vesely |
| 2001/0047150 | A1 | 11/2001 | Chobotov |
| 2002/0013547 | A1 | 1/2002 | Paskar |
| 2003/0208222 | A1 | 11/2003 | Zadno-Azizi |
| 2004/0049207 | A1 | 3/2004 | Goldfarb et al. |
| 2004/0064179 | A1 | 4/2004 | Linder et al. |
| 2004/0116848 | A1 | 6/2004 | Gardeski et al. |
| 2004/0127849 | A1 | 7/2004 | Kantor |
| 2004/0133232 | A1 | 7/2004 | Rosenbluth et al. |
| 2004/0147826 | A1 | 7/2004 | Peterson |
| 2005/0038383 | A1 | 2/2005 | Kelley et al. |
| 2005/0085903 | A1 | 4/2005 | Lau |
| 2005/0131343 | A1 | 6/2005 | Abrams et al. |
| 2005/0137695 | A1 | 6/2005 | Salahieh et al. |
| 2005/0143809 | A1 | 6/2005 | Salahieh et al. |
| 2005/0228290 | A1 | 10/2005 | Borovsky et al. |
| 2005/0256452 | A1 | 11/2005 | DeMarchi et al. |
| 2005/0259452 | A1 | 11/2005 | Cho |
| 2005/0283231 | A1 | 11/2005 | Haug et al. |
| 2005/0277874 | A1 | 12/2005 | Selkee |
| 2005/0277876 | A1 | 12/2005 | Hayden |
| 2005/0288768 | A1 | 12/2005 | Sowinski et al. |
| 2006/0074383 | A1 | 4/2006 | Boulais |
| 2006/0135961 | A1 | 6/2006 | Rosenman et al. |
| 2007/0060997 | A1 | 3/2007 | de Boer |
| 2007/0118155 | A1 | 5/2007 | Goldfarb et al. |
| 2007/0156225 | A1 | 7/2007 | George et al. |
| 2007/0173757 | A1 | 7/2007 | Levine et al. |
| 2007/0197858 | A1 | 8/2007 | Goldfarb et al. |
| 2007/0203561 | A1 | 8/2007 | Forster et al. |
| 2007/0260225 | A1 | 11/2007 | Sakakine et al. |
| 2007/0270779 | A1 | 11/2007 | Jacobs et al. |
| 2007/0299424 | A1 | 12/2007 | Cumming et al. |
| 2008/0058722 | A1 | 3/2008 | Von Oepen et al. |
| 2008/0103585 | A1 | 5/2008 | Monstadt et al. |
| 2008/0109065 | A1 | 5/2008 | Bowe |
| 2008/0188850 | A1 | 8/2008 | Mody et al. |
| 2008/0195126 | A1 | 8/2008 | Solem |
| 2008/0200980 | A1 | 8/2008 | Robin et al. |
| 2008/0243081 | A1* | 10/2008 | Nance ................ A61B 17/3439 604/164.03 |
| 2009/0036768 | A1 | 2/2009 | Seehusen et al. |
| 2009/0069885 | A1 | 3/2009 | Rahdert et al. |
| 2009/0099554 | A1 | 4/2009 | Forster et al. |
| 2009/0163934 | A1 | 6/2009 | Raschdorf, Jr. et al. |
| 2009/0182407 | A1 | 7/2009 | Leanna et al. |
| 2009/0204005 | A1 | 8/2009 | Keast et al. |
| 2009/0240326 | A1 | 9/2009 | Wilson et al. |
| 2009/0276039 | A1 | 11/2009 | Meretei |
| 2009/0281619 | A1 | 11/2009 | Le et al. |
| 2010/0004739 | A1 | 1/2010 | Vesely |
| 2010/0030057 | A1 | 2/2010 | Gavriely et al. |
| 2010/0044410 | A1 | 2/2010 | Argentine et al. |
| 2010/0059173 | A1 | 3/2010 | Kampa et al. |
| 2010/0070009 | A1 | 3/2010 | Barker |
| 2010/0082089 | A1 | 4/2010 | Quadri et al. |
| 2010/0217261 | A1 | 8/2010 | Watson |
| 2010/0249894 | A1 | 9/2010 | Oba et al. |
| 2010/0298931 | A1 | 11/2010 | Quadri et al. |
| 2010/0331776 | A1 | 12/2010 | Salahieh et al. |
| 2011/0112630 | A1 | 5/2011 | Groothuis et al. |
| 2011/0147251 | A1 | 6/2011 | Hodshon et al. |
| 2011/0166566 | A1 | 7/2011 | Gabriel |
| 2011/0166649 | A1 | 7/2011 | Gross et al. |
| 2011/0202128 | A1 | 8/2011 | Duffy |
| 2011/0257718 | A1 | 10/2011 | Argentine |
| 2011/0307049 | A1 | 12/2011 | Kao |
| 2011/0319904 | A1 | 12/2011 | Hollett et al. |
| 2012/0022640 | A1 | 1/2012 | Gross et al. |
| 2012/0065464 | A1 | 3/2012 | Ellis et al. |
| 2012/0109078 | A1* | 5/2012 | Schaeffer .......... A61M 25/0012 604/264 |
| 2012/0172915 | A1 | 7/2012 | Fifer et al. |
| 2012/0316639 | A1 | 12/2012 | Kleinschrodt |
| 2012/0330348 | A1 | 12/2012 | Strauss et al. |
| 2012/0330408 | A1 | 12/2012 | Hillukka et al. |
| 2013/0030514 | A1 | 1/2013 | Kasprzak et al. |
| 2013/0041314 | A1 | 2/2013 | Dillon |
| 2013/0046298 | A1 | 2/2013 | Kaufman et al. |
| 2013/0066342 | A1 | 3/2013 | Dell et al. |
| 2013/0103001 | A1 | 4/2013 | BenMaamer et al. |
| 2013/0109910 | A1 | 5/2013 | Alexander et al. |
| 2013/0110227 | A1 | 5/2013 | Quadri et al. |
| 2013/0131775 | A1 | 5/2013 | Hadley et al. |
| 2013/0289696 | A1 | 10/2013 | Maggard et al. |
| 2014/0088355 | A1 | 3/2014 | Schaeffer |
| 2014/0107693 | A1 | 4/2014 | Plassman |
| 2014/0114390 | A1 | 4/2014 | Tobis et al. |
| 2014/0142688 | A1 | 5/2014 | Duffy et al. |
| 2014/0148889 | A1 | 5/2014 | Deshmukh et al. |
| 2014/0180124 | A1 | 6/2014 | Whiseant et al. |
| 2014/0200649 | A1 | 7/2014 | Essinger et al. |

(56) References Cited

U.S. PATENT DOCUMENTS

| | | |
|---|---|---|
| 2014/0228871 A1 | 8/2014 | Cohen et al. |
| 2014/0276966 A1 | 9/2014 | Ranucci et al. |
| 2014/0324164 A1 | 10/2014 | Gross et al. |
| 2014/0336744 A1 | 11/2014 | Tani et al. |
| 2014/0379074 A1 | 12/2014 | Spence et al. |
| 2015/0005704 A1 | 1/2015 | Heisei et al. |
| 2015/0005801 A1 | 1/2015 | Marquis et al. |
| 2015/0073341 A1 | 3/2015 | Salahieh et al. |
| 2015/0088189 A1 | 3/2015 | Paul, Jr. |
| 2015/0094656 A1 | 4/2015 | Salahieh et al. |
| 2015/0112430 A1 | 4/2015 | Creaven et al. |
| 2015/0272759 A1 | 10/2015 | Argentine |
| 2015/0273181 A1 | 10/2015 | Leeflang et al. |
| 2015/0306806 A1 | 10/2015 | Dando et al. |
| 2016/0045311 A1 | 2/2016 | McCann et al. |
| 2016/0074163 A1 | 3/2016 | Yang et al. |
| 2016/0113765 A1 | 4/2016 | Ganesan et al. |
| 2016/0128819 A1 | 5/2016 | Giordano et al. |
| 2016/0143661 A1 | 5/2016 | Wood et al. |
| 2017/0035566 A1 | 2/2017 | Krone et al. |
| 2017/0042678 A1 | 2/2017 | Ganesan et al. |
| 2017/0080186 A1 | 3/2017 | Salahieh et al. |
| 2017/0232238 A1 | 8/2017 | Biller et al. |
| 2018/0028177 A1 | 2/2018 | von Oepen et al. |
| 2018/0028215 A1 | 2/2018 | Cohen |
| 2018/0028305 A1 | 2/2018 | von Oepen et al. |
| 2018/0028787 A1 | 2/2018 | McNiven et al. |
| 2018/0055636 A1 | 3/2018 | Valencia et al. |
| 2018/0055637 A1 | 3/2018 | von Oepen et al. |
| 2018/0056033 A1 | 3/2018 | von Oepen et al. |
| 2018/0056043 A1 | 3/2018 | von Oepen et al. |
| 2018/0071098 A1* | 3/2018 | Alon ................ A61F 2/2412 |
| 2018/0092744 A1 | 4/2018 | von Oepen et al. |
| 2018/0126119 A1 | 5/2018 | McNiven et al. |
| 2018/0132837 A1 | 5/2018 | Mathena et al. |
| 2018/0133454 A1 | 5/2018 | von Oepen et al. |
| 2018/0360457 A1 | 12/2018 | Ellis et al. |
| 2019/0015086 A1* | 1/2019 | Blumenthal ........ A61B 17/0057 |
| 2019/0030285 A1 | 1/2019 | Prabhu et al. |
| 2019/0274831 A1 | 9/2019 | Prabhu |
| 2020/0230352 A1 | 7/2020 | Mcniven et al. |
| 2020/0230354 A1 | 7/2020 | Von Oepen et al. |

FOREIGN PATENT DOCUMENTS

| | | |
|---|---|---|
| CN | 1859942 A | 11/2006 |
| CN | 1961983 A | 5/2007 |
| CN | 101247847 A | 8/2008 |
| CN | 101426452 A | 5/2009 |
| CN | 101479006 A | 7/2009 |
| CN | 101506538 A | 8/2009 |
| CN | 102159277 A | 8/2011 |
| CN | 102258402 A | 11/2011 |
| CN | 102405022 A | 4/2012 |
| CN | 102481433 A | 5/2012 |
| CN | 102548505 A | 7/2012 |
| CN | 102770080 | 11/2012 |
| CN | 102933161 A | 2/2013 |
| CN | 103517689 A | 1/2014 |
| CN | 103702635 A | 4/2014 |
| CN | 103841899 | 6/2014 |
| CN | 103957993 A | 7/2014 |
| CN | 104203329 A | 12/2014 |
| CN | 104812439 A | 7/2015 |
| CN | 105246434 A | 1/2016 |
| CN | 105899167 A | 8/2016 |
| EP | 0989882 A1 | 4/2000 |
| EP | 1980288 | 10/2008 |
| EP | 2529701 A1 | 12/2012 |
| EP | 2537487 | 12/2012 |
| EP | 2702965 | 3/2014 |
| EP | 3009103 | 4/2016 |
| JP | 06-343702 A | 12/1994 |
| JP | 2003062072 | 3/2003 |
| JP | 2006528911 | 12/2006 |
| JP | 2013516244 | 5/2013 |
| WO | WO 2001051114 | 7/2001 |
| WO | WO 2007044285 | 4/2007 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | 2011/033783 A1 | 3/2011 |
| WO | WO 2012020521 | 2/2012 |
| WO | 2012/057983 A1 | 5/2012 |
| WO | WO 2012151396 | 11/2012 |
| WO | 2013/006282 A1 | 1/2013 |
| WO | 2013/126529 A2 | 8/2013 |
| WO | WO 2014064694 | 5/2014 |
| WO | WO 2014121280 | 8/2014 |
| WO | WO 2014128705 | 8/2014 |
| WO | WO 2015191938 | 12/2015 |
| WO | WO 2016022797 | 2/2016 |
| WO | WO 2016112085 | 7/2016 |
| WO | WO 2016144708 | 9/2016 |
| WO | WO 2016150806 | 9/2016 |
| WO | WO 2016183526 | 11/2016 |
| WO | 2017/023534 A2 | 2/2017 |
| WO | WO 2018023038 | 2/2018 |
| WO | WO 2018023043 | 2/2018 |
| WO | WO 2018023044 | 2/2018 |
| WO | WO 2018023045 | 2/2018 |
| WO | WO 2018023052 | 2/2018 |
| WO | WO 2018044446 | 3/2018 |
| WO | WO 2018044447 | 3/2018 |
| WO | WO 2018044448 | 3/2018 |
| WO | WO 2018044449 | 3/2018 |
| WO | WO 2018067788 | 4/2018 |
| WO | WO 2018093426 | 5/2018 |

OTHER PUBLICATIONS

U.S. Appl. No. 15/662,001, Jun. 20, 2019, OA.
U.S. Appl. No. 15/662,001, Oct. 4, 2019, OA.
U.S. Appl. No. 15/662,001, Dec. 18, 2019, Notice of Allowance.
U.S. Appl. No. 15/662,001, Mar. 24, 2020 Notice of Allowance.
U.S. Appl. No. 15/662,008, Sep. 13, 2019, Office Action.
U.S. Appl. No. 15/662,008, Jan. 31, 2020, Notice of Allowance.
U.S. Appl. No. 15/662,013, Jun. 13, 2019, Office Action.
U.S. Appl. No. 15/662,013, Oct. 10, 2019, Office Action.
U.S. Appl. No. 15/662,013, Dec. 5, 2019, Advisory Action.
U.S. Appl. No. 15/662,013, May 7, 2020, Notice of Allowance.
U.S. Appl. No. 15/662,014, May 31, 2019, Office Action.
U.S. Appl. No. 15/662,014, Oct. 2, 2019, Notice of Allowance.
U.S. Appl. No. 15/662,014, Jan. 23, 2020, Notice of Allowance.
U.S. Appl. No. 15/662,066, Jul. 11, 2019, Office Action.
U.S. Appl. No. 15/662,066, Dec. 16, 2019, Office Action.
U.S. Appl. No. 15/662,066, Feb. 27, 2020, Advisory Action.
U.S. Appl. No. 15/662,076, Oct. 8, 2019, Notice of Allowance.
U.S. Appl. No. 15/662,076, Jan. 31, 2020, Notice of Allowance.
U.S. Appl. No. 15/662,089, Oct. 7, 2019, Office Action.
U.S. Appl. No. 15/662,089, Jan. 10, 2020, Office Action.
U.S. Appl. No. 15/662,093, Mar. 7, 2019, Office Action.
U.S. Appl. No. 15/662,093, Aug. 29, 2019, Office Action.
U.S. Appl. No. 15/662,093, Dec. 3, 2019, Office Action.
U.S. Appl. No. 15/662,093, May 6, 2020, Office Action.
U.S. Appl. No. 15/662,098, Jul. 5, 2019, Office Action.
U.S. Appl. No. 15/662,098, Jan. 27, 2020, Office Action.
U.S. Appl. No. 15/662,098, Mar. 23, 2020, Advisory Action.
U.S. Appl. No. 15/662,098, Apr. 30, 2020, Office Action.
U.S. Appl. No. 15/662,066, May 21, 2020, Office Action.
U.S. Appl. No. 15/662,142, Dec. 20, 2019, Advisory Action.
U.S. Appl. No. 15/662,142, Apr. 17, 2020, Office Action.
U.S. Appl. No. 15/724,499, Jul. 15, 2019, Notice of Allowance.
U.S. Appl. No. 15/724,499, Aug. 27, 2019, Supplemental Notice of Allowance.
U.S. Appl. No. 15/724,499, Nov. 22, 2019, Supplemental Notice of Allowance.
U.S. Appl. No. 15/724,499, Mar. 25, 2020, Office Action.

(56) References Cited

OTHER PUBLICATIONS

Advisory Action received for U.S. Appl. No. 15/662,093, dated Jul. 9, 2020.
Notice of Allowance received for U.S. Appl. No. 15/724,499, dated Jul. 1, 2020.
Office Action received for U.S. Appl. No. 15/662,089, dated Jun. 11, 2020.

* cited by examiner

INTRAVASCULAR DELIVERY SYSTEM

CROSS-REFERENCE TO RELATED APPLICATIONS

This application claims priority to and the benefit of U.S. Provisional Patent Application Ser. No. 62/768,446, filed Nov. 16, 2018 and titled "INTRAVASCULAR DELIVERY SYSTEM," the entirety of which is incorporated herein by this reference.

BACKGROUND

1. Field of the Invention

The present disclosure generally relates to devices, systems, and methods for delivering an interventional device to targeted anatomy such as at the mitral annulus.

2. The Relevant Technology

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication.

An example of an intravascular procedure that significantly reduces procedure and recovery time and cost over conventional open surgery is a heart valve replacement or repair procedure in which an artificial valve or valve repair device is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more deflecting mechanisms, which can be achieved by tension cable, or other mechanisms positioned inside the catheter. Precise control of the distal end of the catheter allows for more reliable and faster positioning of a medical device and/or implant and other improvements in the procedures.

An intravascularly delivered device needs to be placed precisely to ensure a correct positioning of the medical device, which is essential for its functionality, as the device may be difficult to reposition after the device is fully deployed from the delivery system. Additionally, the ability to recapture a partially deployed device is desirable in the event that the distal end of the catheter moves relative to the target location and compromises the precise positioning of the device.

SUMMARY

Embodiments of the present disclosure solve one or more problems in the art with systems, methods, and devices for intravascular delivery of an interventional device to targeted intravascular anatomy, including a targeted cardiac valve. Suitable interventional devices that may be utilized in conjunction with the delivery system embodiments described herein may include valve repair devices, annuloplasty devices, valve clip devices, artificial heart valve devices, and other interventional devices. Embodiments described herein may be particularly useful for delivering interventional devices that move from a compressed, pre-deployed state to an expanded, deployed state.

In one embodiment, a delivery system includes an elongate delivery member having a proximal end and a distal end configured for housing the interventional device, and including a plurality of coaxially positioned delivery member components. The delivery member components include a delivery catheter and an inner catheter (i.e., suture catheter) coaxially positioned within the delivery catheter. The inner catheter is adapted to maintain a connection with the interventional device until deployment of the interventional device.

The delivery system also includes a handle assembly for controlling movement of the delivery catheter and inner catheter. The handle assembly includes a delivery catheter holder to which a proximal end of the delivery catheter is attached, an inner catheter holder to which a proximal end of the inner catheter is attached, the inner catheter holder being disposed proximal of the delivery catheter holder, and a mechanical linkage (e.g., a lead rod) that fixes the relative positions of the delivery catheter holder and the inner catheter holder. The mechanical linkage enables the delivery catheter and the inner catheter to translate together relative to one or more other components of the delivery member.

The inner catheter holder includes a quick-release mechanism configured to enable selective decoupling of the inner catheter holder from the mechanical linkage to enable the inner catheter holder to move relative to the delivery catheter holder. The quick-release mechanism may be a pin that is biased toward the fixed, locked position by a spring. Depressing the pin, or a cap positioned thereon, causes the pin to disengage with the mechanical linkage so that the user can slide the inner catheter holder and thereby adjust the position of the inner catheter relative to the delivery catheter.

In another embodiment, a delivery system includes an interventional device formed from nitinol, and an elongated delivery member. The elongated delivery member includes a proximal end, a distal end, and an outer sheath. The outer sheath forms an interventional device cover configured to house the interventional device and maintain the interventional device in a compressed, pre-deployed state. The outer sheath is longitudinally translatable relative to the interventional device.

A portion of the interventional device may be biased against an inner surface of the cover when the interventional device is housed within the cover. Beneficially, the interventional device cover is formed from titanium and is resistant to scratching from the interventional device caused by longitudinal translation of the outer sheath relative to the interventional device. A titanium cover also limits potential contamination of the nitinol interventional device housed therein.

The cover may have a wall thickness of about 0.2 mm to about 0.5 mm, or about 0.3 mm to about 0.4 mm, and may be sufficiently echotransparent to enable echocardiographic visualization of the interventional device while the device is housed within the cover.

In another embodiment, a delivery system includes a steering catheter that includes a laser cut hypotube. A tip ring is attached to the distal end of the hypotube. The tip ring includes a step formed within the interior of its proximal end. The step forms a first inner diameter of the tip ring that matches or is slightly larger than an outer diameter of the hypotube such that the hypotube may be inserted into the proximal end of the tip ring. The tip ring has a second inner diameter distally beyond the step, extending to the distal end of the tip ring, that is substantially equal to the inner diameter of the hypotube. The step provides a substantially smooth transition between the inner diameter of the hypotube and the second inner diameter of the tip ring.

In another embodiment, a delivery system includes a steering catheter with a gradient bend cut pattern disposed along at least a portion thereof (e.g., a distal portion). The cut pattern defines a preferred bending direction of the steering catheter. The cut pattern includes a series of island cuts aligned on a first side of the steering catheter and a series of corresponding slits on a second, opposite side of the steering catheter that enable the steering catheter to preferentially bend toward the first side and away from the second side. The cut pattern is arranged such that the island cuts become progressively smaller toward the distal end of the steering catheter.

In another embodiment, a delivery system includes a delivery catheter having features that limit friction of the delivery catheter against an outer member when translating within the outer member. The delivery system includes an outer member and a delivery catheter disposed within the outer member. The delivery catheter is longitudinally translatable within the outer member. At least the distal section of the delivery catheter includes a coil section and a braid section surrounding the coil section and attached thereto. The braid section is attached to the coil section with sufficient slack to allow the distal section of the delivery catheter to bend about 0° to about 180°, 180° to about 540°, or about 270° to about 360°.

In another embodiment, a delivery system includes an elongated delivery member coupled to a handle assembly and extending distally from the handle assembly. The delivery member includes an outer member and a delivery catheter concentrically disposed within the outer member. The delivery member includes a can structure disposed at its distal end. The can structure is configured to at least partially house an interventional device within the can structure and to maintain the interventional device in a compressed, pre-deployed state. The can structure can include a cut pattern providing preferential bending of the can structure along at least one plane.

In some embodiments, the can structure includes a proximal section and a distal section separated by a divider. The cut pattern may be located on the proximal section. The delivery catheter may extend through the proximal section of the can structure and couple to the can structure at the divider. The can structure may be formed of titanium or a titanium alloy.

The embodiments summarized above are each combinable with one another. Some embodiments may utilize one or more components of any of the embodiments summarized above and described in greater detail below.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Delivery System Overview

Figure 1:
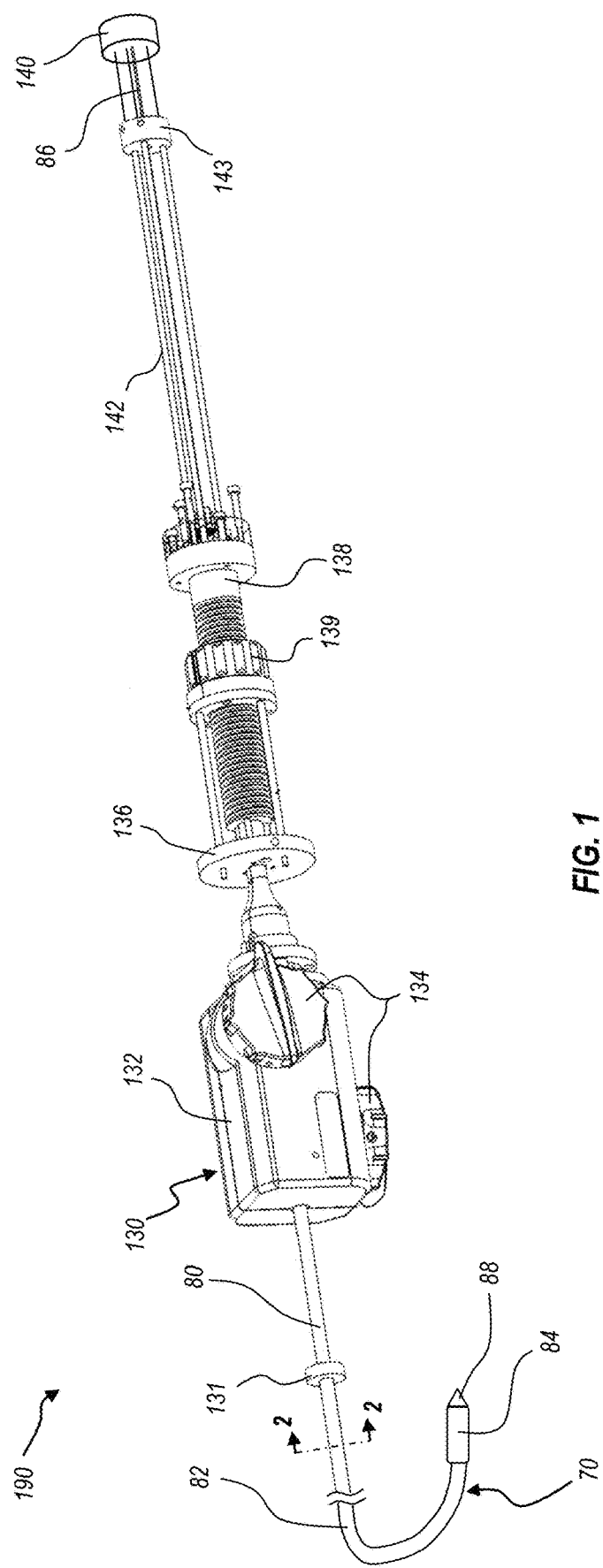
FIG. 1 illustrates a delivery system configured for delivering, positioning, and deploying an interventional device, the delivery system including a handle assembly coupled to a delivery member.

FIG. 1 illustrates an exemplary embodiment of a delivery system 190. As shown, the delivery system 190 includes a handle assembly 130 and a delivery member 70. The delivery member 70 is coupled to the handle assembly 130 and extends distally from the handle assembly 130. The delivery member 70 includes a plurality of catheter and/or hypotube members which provide different functionality during operation of the delivery system 190 to enable effective delivery and deployment of an interventional device.

The proximal end of an outer sheath 82 is coupled to an end ring 131, and the outer sheath 82 extends to a distal tip 88. A steering catheter handle 132 is disposed proximal of the end ring 131. The proximal end of a steering catheter 80 is coupled to the steering catheter handle 132, and the steering catheter 80 extends distally from the steering catheter handle 132 into the outer sheath 82. The steering catheter handle 132 includes one or more controls 134 which are operatively coupled to the steering catheter so that manipulation of the controls 134 adjusts the curvature of the steering catheter 80.

The outer sheath 82 extends to a distal end where it is coupled to a distal piece 84 (which may also be referred to herein as a "valve cover 84"). The distal piece 84 functions to house an interventional device in a compressed, pre-deployed state during intravascular delivery of the device to the targeted cardiac site.

Because the steering catheter 80 is nested within the outer sheath 82, curving of the steering catheter 80 causes corresponding curving/steering in the outer sheath 82. The steering catheter 80 and outer sheath 82 may be referred to singly or collectively herein as the "outer member." The illustrated embodiment of the delivery member 70 includes additional components which are not visible in the view of FIG. 1 but may be seen in the cross-sectional view of FIG. 2.

Figure 2:
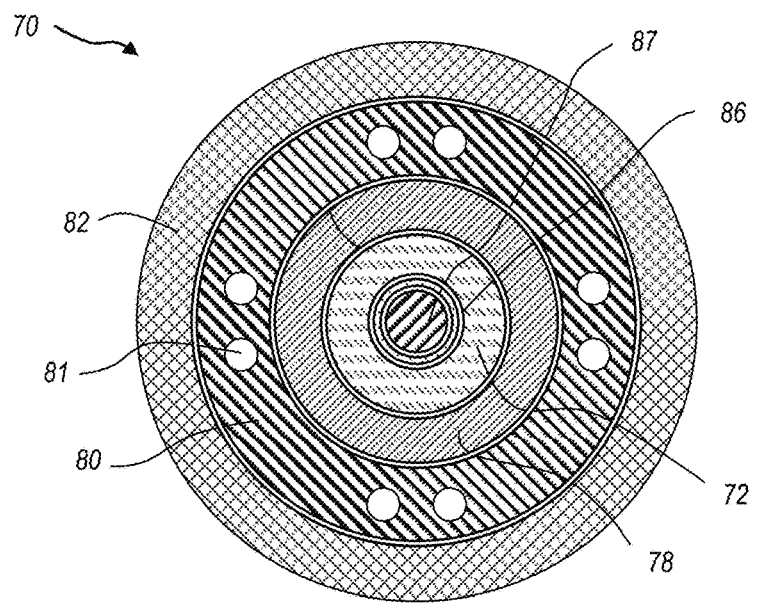
FIG. 2 illustrates a cross-sectional view of the delivery member showing various delivery member components that may be utilized, including a steering catheter and a delivery catheter disposed within and translatable within the steering catheter.

FIG. 2 illustrates a cross-sectional view of the delivery member 70 taken along the cross-section line 2-2. As shown, the steering catheter 80 is disposed within the outer sheath 82. A delivery catheter 78 (or alternatively referred to herein as an extension catheter) is disposed within the steering catheter 80. An inner catheter 72 (also referred to herein as suture catheter 72) may be disposed within the delivery catheter 78, and a guidewire tube 86 may be disposed within the inner catheter 72. The guidewire tube 86 is configured for receiving a guidewire 87. Although the particular nested configuration shown in FIG. 2 represents one preferred embodiment, alternative embodiments may include a different concentric arrangement of constituent parts. For example, some embodiments may combine the steering catheter 80 and outer sheath 82 and/or configure the outermost member with steering functionality, some embodiments may include more than one catheter with steering functionality, etcetera.

The steering catheter 80 is configured to be selectively curved to allow intravascular navigation. In some embodiments, the steering catheter 80 provides steerability via a plurality of lumens 81 extending through the length of the steering catheter 80. The lumens 81 may be configured for receiving tension cables which extend between the controls 134 and the distal end of the steering catheter 80. One or more tension cables may additionally or alternatively be coupled to intermediate sections of the steering catheter 80. Manipulation of the controls 134 therefore adjusts tension in the tension cables to increase or decrease curvature of the steering catheter 80 at various positions. Although the controls 134 are shown here as knobs, alternative embodiments may additionally or alternatively include one or more buttons, sliders, ratcheting mechanisms, or other suitable controls capable of adjusting tension to provide steering. Illustrative structures that can be used as part of the steering catheter handle 132 and or steering catheter 80 are described in U.S. Pat. No. 7,736,388, which is incorporated herein by this reference.

Referring again to FIG. 1, a delivery catheter holder 136 is disposed proximal of the steering catheter handle 132. Although not visible in the view of FIG. 1, the proximal end of the delivery catheter 78 is coupled to the delivery catheter holder 136. The delivery catheter 78 extends distally away from the delivery catheter holder 136 and into the steering catheter 80. An inner catheter holder 138 (also referred to herein as suture catheter holder 138) is disposed proximal of the delivery catheter holder 136. The inner catheter 72 may be coupled to the inner catheter holder 138 so that translation of the inner catheter holder 138 corresponds to translation of the inner catheter 72. For example, the inner catheter 72 may be selectively locked relative to the inner catheter holder 138 through a set screw, clamp, or other selective holding mechanism. The inner catheter 72 extends distally away from the inner catheter holder 138 and into the delivery catheter 78.

An inner catheter control 139 is operatively coupled to the inner catheter holder 138. Manipulation of the inner catheter control 139 adjusts the relative positioning of the delivery catheter holder 136 and inner catheter holder 138, and thus the relative positioning of the delivery catheter 78 and the inner catheter 72. In the illustrated embodiment, the inner catheter control 139 operates through threaded engagement with the inner catheter holder 138, such that rotation of the inner catheter control 139 translates the inner catheter holder 138 relative to the control 139 and therefore relative to the delivery catheter holder 136. Alternative embodiments may additionally or alternatively include one or more of a slider and rail assembly, a ratcheting mechanism, or other suitable means of linear adjustment.

The inner catheter 72 may extend proximally to and be attached to an inner catheter cap 143. A user may decouple the inner catheter 72 from the inner catheter holder 138 to allow movement of the inner catheter 72 by sliding/translating the inner catheter cap 143 along alignment rods 142. The guidewire tube 86 extends distally through the alignment cap 143 and into the inner catheter 72. The guidewire tube 86 extends to the distal end of the delivery member 70 where it is attached to a distal tip 88. The distal tip 88 is preferably formed from a flexible polymer material and provides an angled, atraumatic shape which assists in passing the delivery member 70 across the inter-atrial septum to the mitral annulus, which is required in a typical transfemoral approach to the mitral annulus.

In the illustrated embodiment, the guidewire tube 86 is coupled to a guidewire tube holder 140. By moving the guidewire tube handle, the guidewire tube 86 may be selectively translatable relative to the inner catheter cap 143 such that the guidewire tube 86 and distal tip 88 may be linearly translated relative to the inner catheter 72 and other components of the delivery member 70. The guidewire tube 86 may be selectively locked in longitudinal position relative to the inner catheter holder 138 and/or inner catheter cap 143, such as through a set screw, clamp, or other selective fastener. For example, such a fastening structure may be associated with the inner catheter cap 143.

When unlocked, the guidewire tube 86 (and likewise the distal tip 88) may be moved relative to the inner catheter 72. The ability to retract the distal tip 88 relative to the inner catheter 72 reduces the risk that the distal tip 88 will become overextended during deployment, where it could become tangled in chordae tendineae and/or cause injury to cardiac tissue. Additionally, independent movement of the guidewire tube 86 (with the distal tip 88) also allows for closing the gap between the distal tip 88 and the valve cover 84 following deployment of the intravascular device. When the intravascular device has been released, the distal tip 88 is separated from the valve cover 84 by a distance, such as by about 40 mm. To avoid drawing air into the catheter, the gap between valve cover 84 and distal tip 88 is closed by drawing the distal tip 88 towards the valve cover 88, preferably in the left side of the heart, to avoid sucking air into the catheter when pulled back into the right side of the heart (where there is relatively low pressure).

Figure 3:
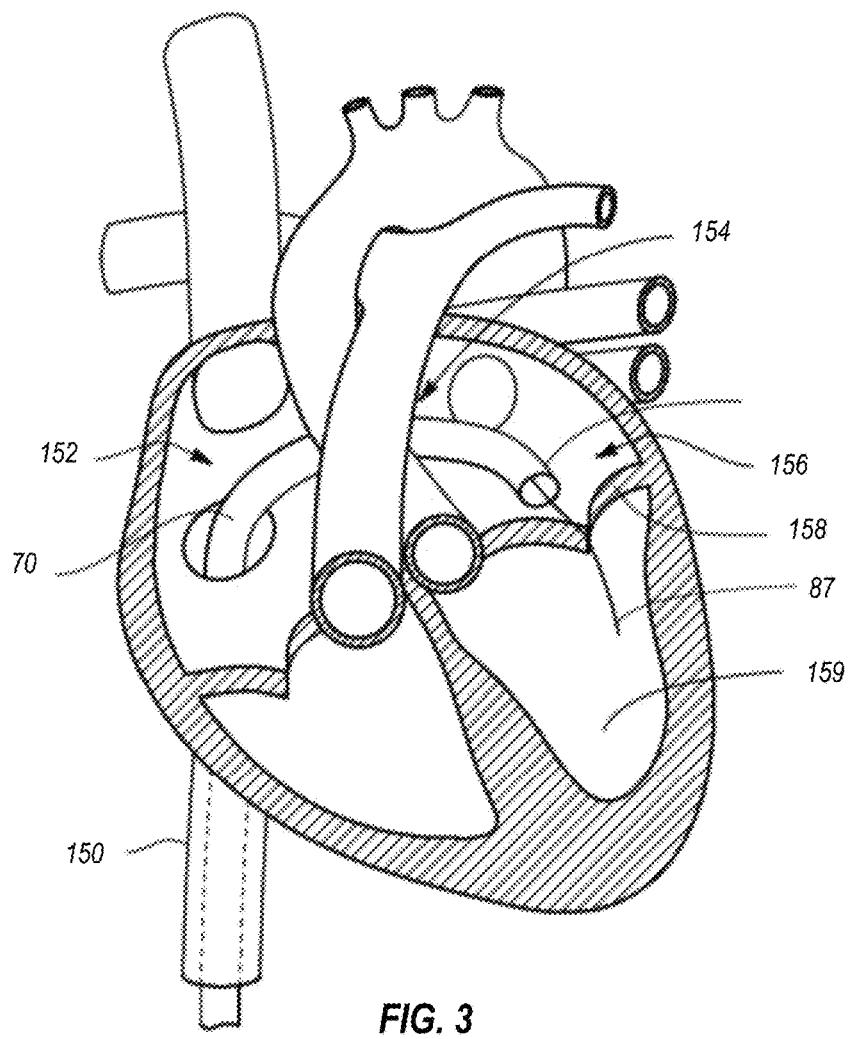
FIG. 3 illustrates an exemplary approach for delivering an interventional device to the mitral annulus.

FIG. 3 illustrates a schematic representation of a patient's heart and a delivery procedure to the mitral annulus that may be conducted using the illustrated delivery system 190. The delivery member 70 may be inserted into the patient's vasculature (e.g., through a transfemoral approach) and directed to the inferior vena cava 150. The delivery member 70 is passed through the inferior vena cava 150 toward the heart. Upon entering the heart from the inferior vena cava 150, the delivery member 70 enters the right atrium 152. For mitral valve related procedures, the delivery member 70 must further pass into the left atrium 156 by passing through a puncture in the intra-atrial septum 154.

In other implementations, such as for procedures associated with a tricuspid valve, the delivery member 70 may be passed through the inferior vena cava 150 and into the right atrium 152, where it may then be positioned and used to perform the procedure related to the tricuspid valve. As described above, although many of the examples described herein relate to delivery to the mitral valve, one or more embodiments may be utilized in other cardiac procedures, including those involving the tricuspid valve.

Although a transfemoral approach for accessing a targeted cardiac valve is one preferred method, it will be understood that the embodiments described herein may also be utilized where alternative approaches are used. For example, embodiments described herein may be utilized in a transjugular approach, transapical approach, or other suitable approach to the targeted anatomy. For procedures related to the mitral valve or tricuspid valve, delivery of the replacement valve or other interventional device is preferably carried out from an atrial aspect (i.e., with the distal end of the delivery member 70 positioned within the atrium superior to the targeted valve). The illustrated embodiments are shown from such an atrial aspect. However, it will be understood that the interventional device embodiments described herein may also be delivered from a ventricular aspect.

In some embodiments, a guidewire 87 is utilized in conjunction with the delivery member 70. For example, the guidewire 87 (e.g., 0.014 in, 0.018 in, 0.035 in) may be routed through the guidewire tube 86 of the delivery member 70 to the targeted cardiac valve.

Additional details regarding delivery systems and devices that may be utilized in conjunction with the components and features described herein are described in United States Patent Application Publication Numbers 2018/0028177A1 and 2018/0092744A1, which are incorporated herein by this reference.

Operation of the Handle Assembly

Figure 4A:
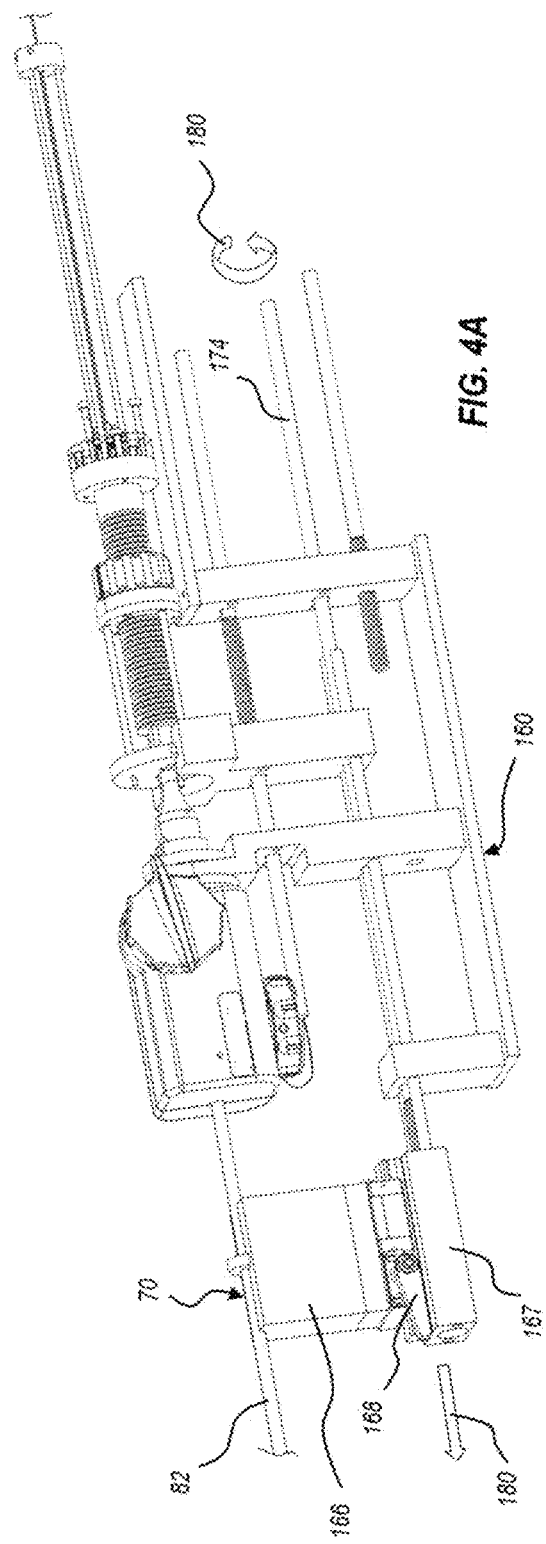
FIGS. 4A through 7B illustrate various operations of the handle assembly to move components of the delivery member relative to one another.
Figure 4B:
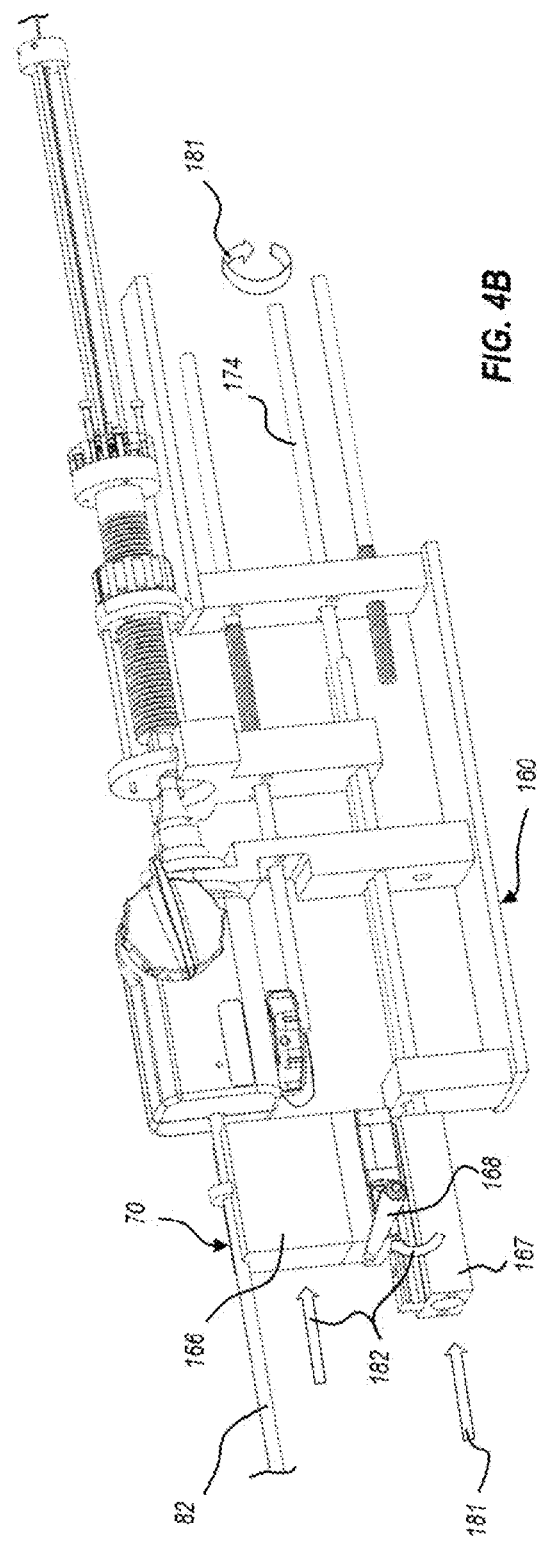

FIGS. 4A and 4B illustrate in greater detail operation of the handle assembly for translating the outer sheath 82. Sheath movement may be utilized to deploy an interventional device sheathed at or otherwise attached to the distal end of the outer sheath 82, or to recapture such an interventional device by advancing the outer sheath 82 over the device. The illustrated embodiment provides two modes for translating the outer sheath 82. The outer sheath adjustor 174 and the slider block 167 are coupled to each other with corresponding threads, and rotation of the outer sheath adjustor 174 causes the slider block 167 to translate. With the slider lock 168 engaged, the outer sheath support 166 and outer sheath 82 move with the slider block 167. The slider lock 168 may also be disengaged, allowing the outer sheath support 166 and outer sheath 82 to be manually advanced or retracted by sliding relative to the slider block 167.

As shown by corresponding arrows 180, rotation of the outer sheath adjustor 174 in one direction causes the slider block 167 to advance, and as shown by corresponding arrows 181, rotation of the outer sheath adjustor 174 in the opposite direction causes the slider block 167 to retract. In FIG. 4A, the slider lock 168 is in an engaged position. In FIG. 4B, arrows 182 show disengagement of the slider lock 168 and translation of the outer sheath support 166 upon the slider block 167. The dual mode adjustment of the outer sheath 82 beneficially allows a user to make different types of adjustments depending on procedural circumstances and/or preferences. For example, a user may make larger, quicker adjustments by unlocking the slider lock 168 and manually sliding the outer sheath support 166, and may make finer, more controlled adjustments by rotation of the outer sheath adjustor 174.

Figure 5A:
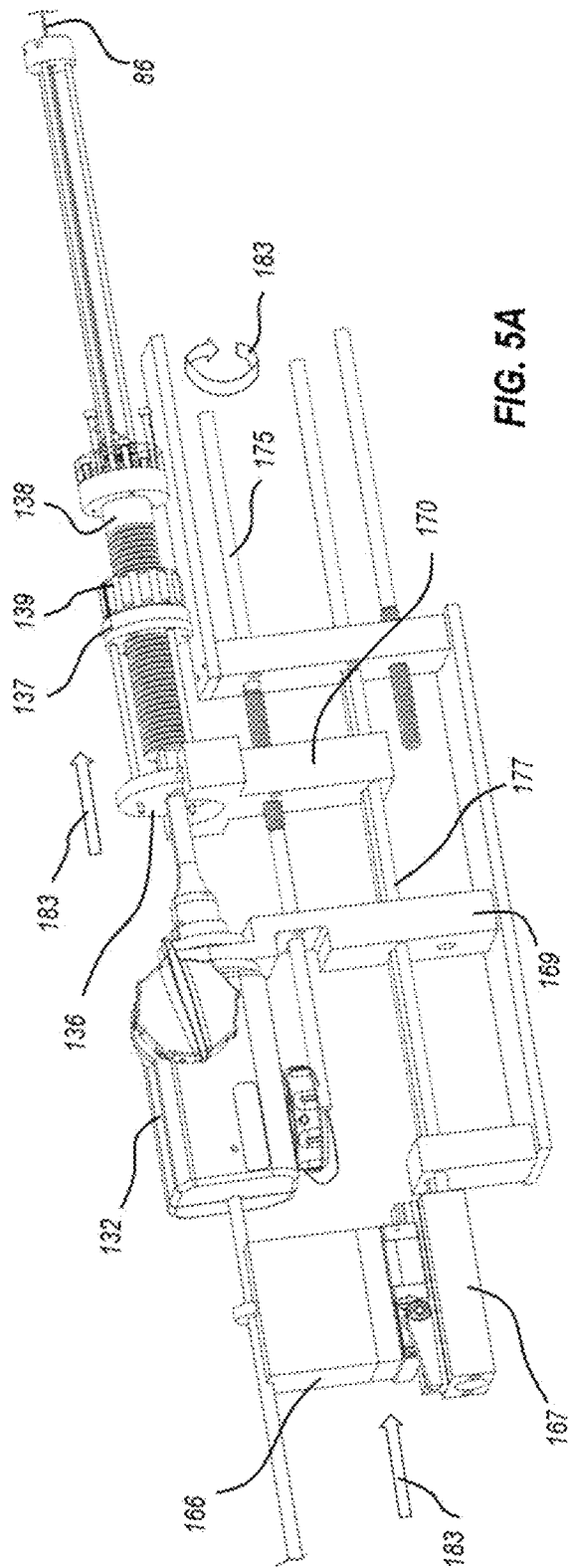
Figure 5B:
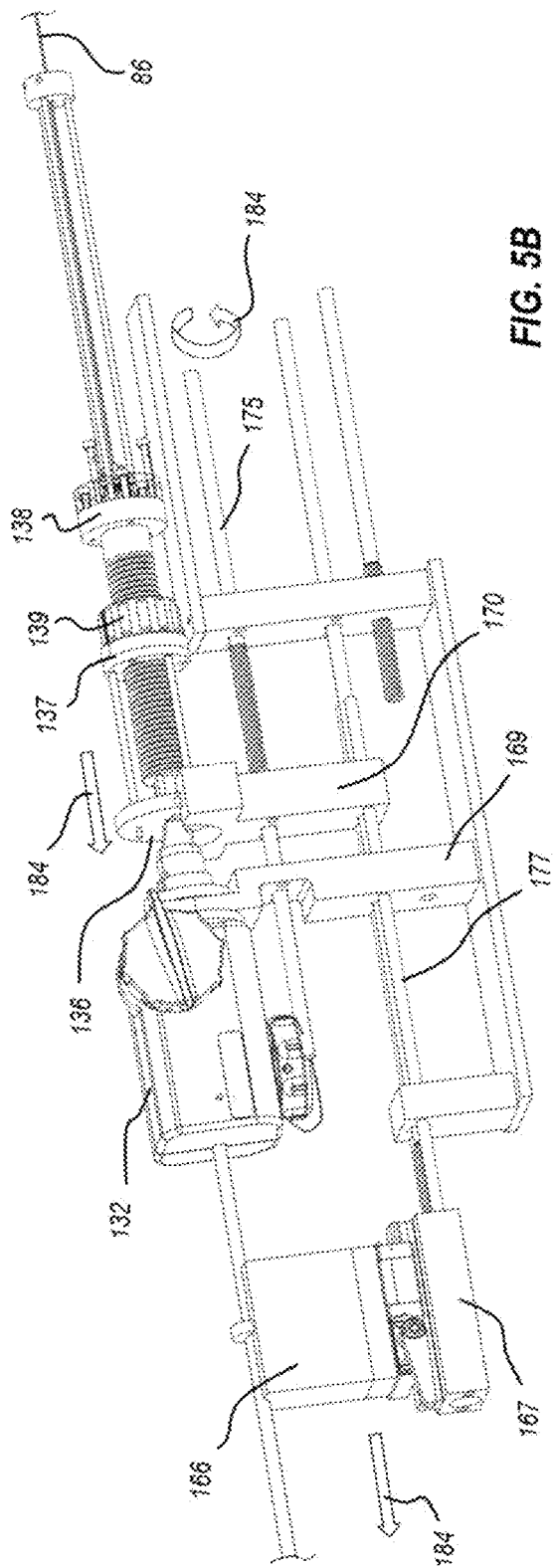

FIGS. 5A and 5B illustrate a deployment adjustment that moves several of the delivery member components relative to the steering catheter 80. FIG. 5A illustrates, by arrows 183, rotation of the deployment adjustor 175 in a first direction to retract the slider block 167, delivery catheter holder 136, and suture catheter holder 138. FIG. 5B illustrates, by arrows 184, rotation of the deployment adjustor 175 in a second direction to advance the slider block 167, deployment catheter holder 136, and suture catheter holder 138. As explained below, after the steering catheter 80 has been curved to orient the delivery member 70 with respect to the mitral annulus, the other components of the delivery member 70 will need to be advanced over the steering catheter 80 to move into a proper position for deployment of the interventional device. Holding the steering catheter 80 in place while the other components are advanced allows the compound curve of the steering catheter 80 to remain in the desired position.

The deployment adjustor 175 is threadedly engaged with the delivery catheter support 170. The connecting rods 177 mechanically link the delivery catheter support 170 to the slider block 167 to form a bracket assembly. The connecting rods 177 are able to freely pass through the steering catheter handle support 169 without engaging. The delivery catheter holder 136 and the suture catheter holder 138 are also mechanically linked as part of the bracket assembly by way of the alignment ring 137 and suture catheter control 139. Accordingly, rotation of the deployment adjustor 175 causes the delivery catheter holder 136, slider block 167, and suture catheter holder 138 to translate while the position of the steering catheter handle 132 is maintained. Translation of the outer sheath support 166 can be assured by locking to the slider block 167.

Figure 6A:
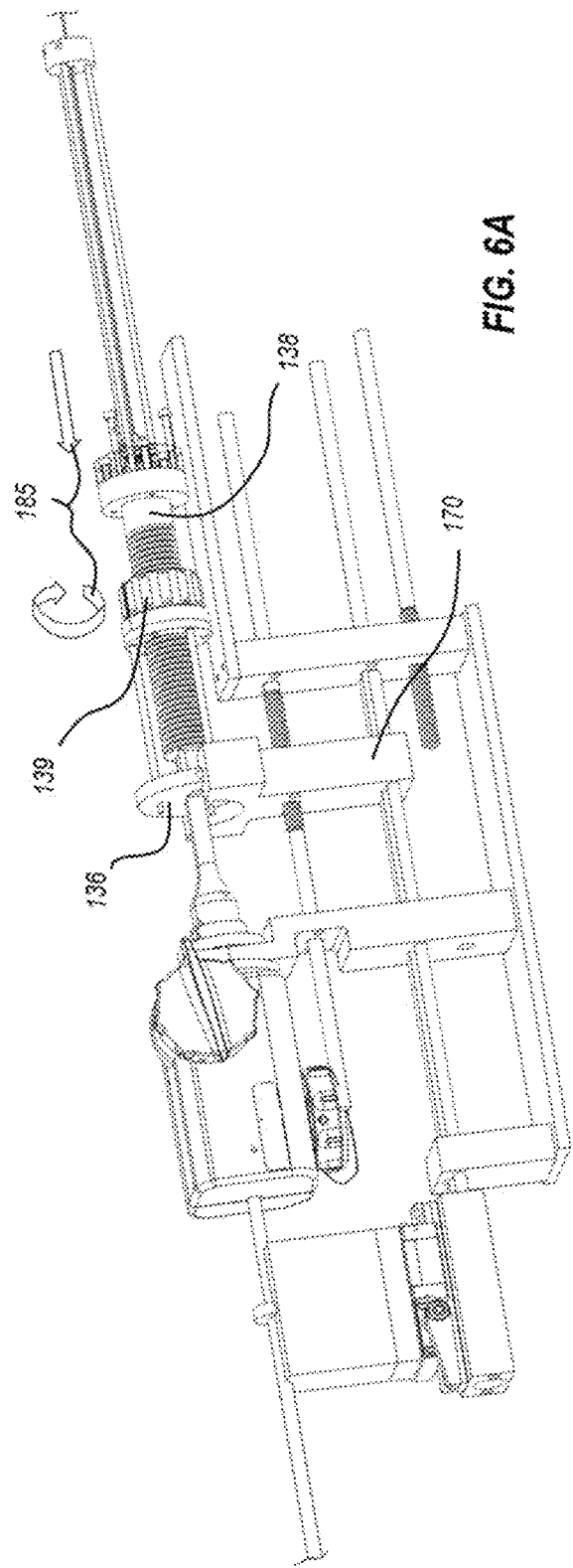
Figure 6B:
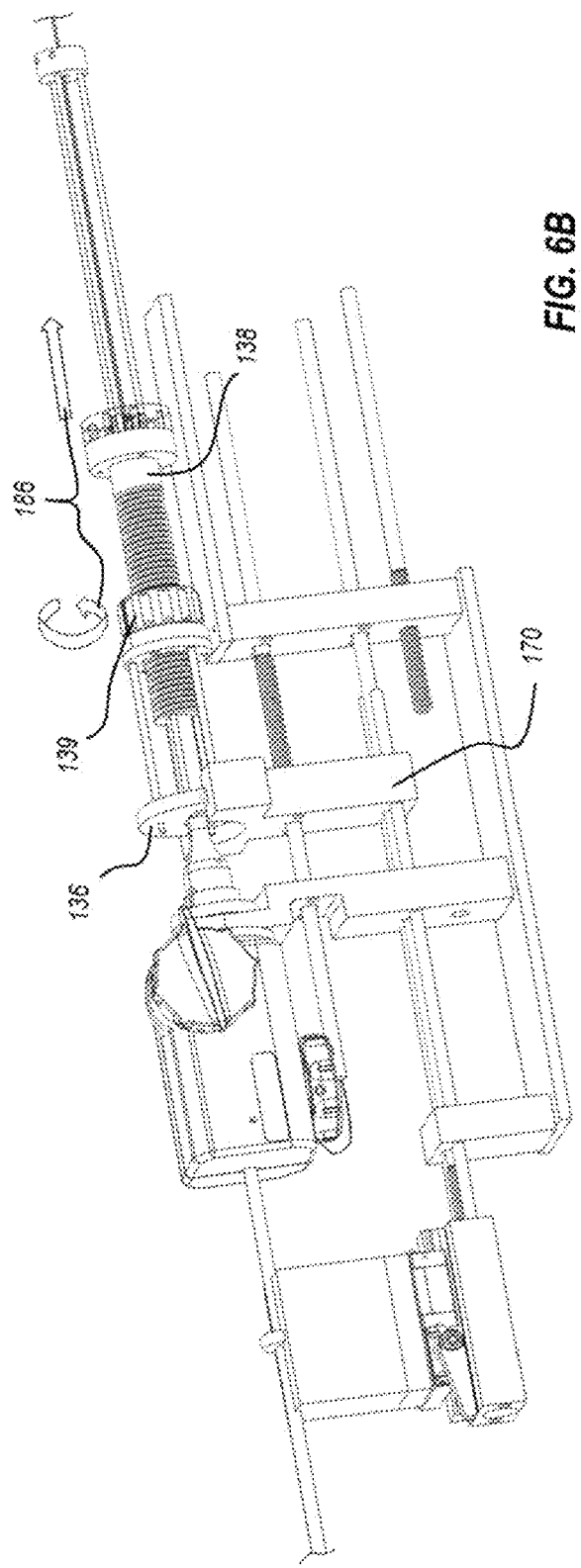

FIGS. 6A and 6B illustrate an operation for moving the suture catheter holder 138 relative to the delivery catheter holder 136. FIG. 6A shows, by arrows 185, that rotation of the suture catheter control 139 in a first direction causes the suture catheter holder 138 to advance relative to the delivery catheter holder 136. FIG. 6B shows, by arrows 186, that rotation of the suture catheter control 139 in a second direction causes the suture catheter holder 138 to retract relative to the delivery catheter holder 136. The threaded engagement of the suture catheter control 139 to the suture catheter holder 138 allows for finely controlled adjustments of the suture catheter position. As explained in more detail below, sutures of the suture catheter 72 (inner catheter 72) may be coupled to an interventional device while the device is in a pre-deployed state, and movement of the suture catheter 72 relative to the delivery catheter 78 allows tension of the sutures to be adjusted.

Other embodiments that may be utilized in addition to or as an alternative to the suture catheter holder 138 and the suture catheter control 139 are provided below in the section titled "Quick-Release Control for Suture Catheter" and are also shown in part by FIGS. 17A and 17B.

Figure 7A:
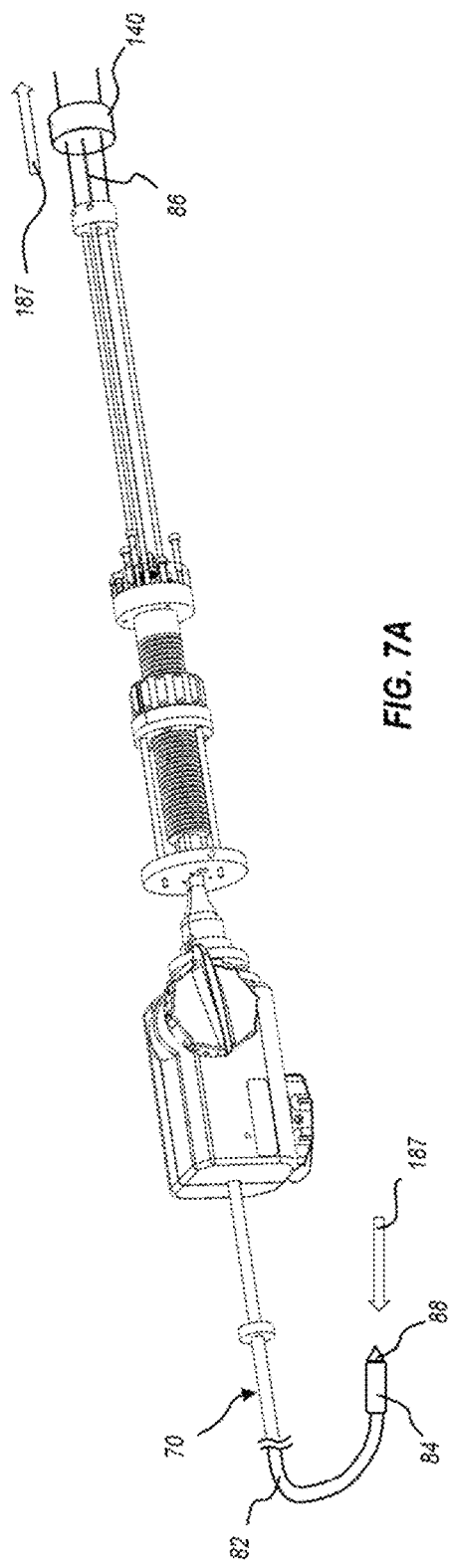
Figure 7B:
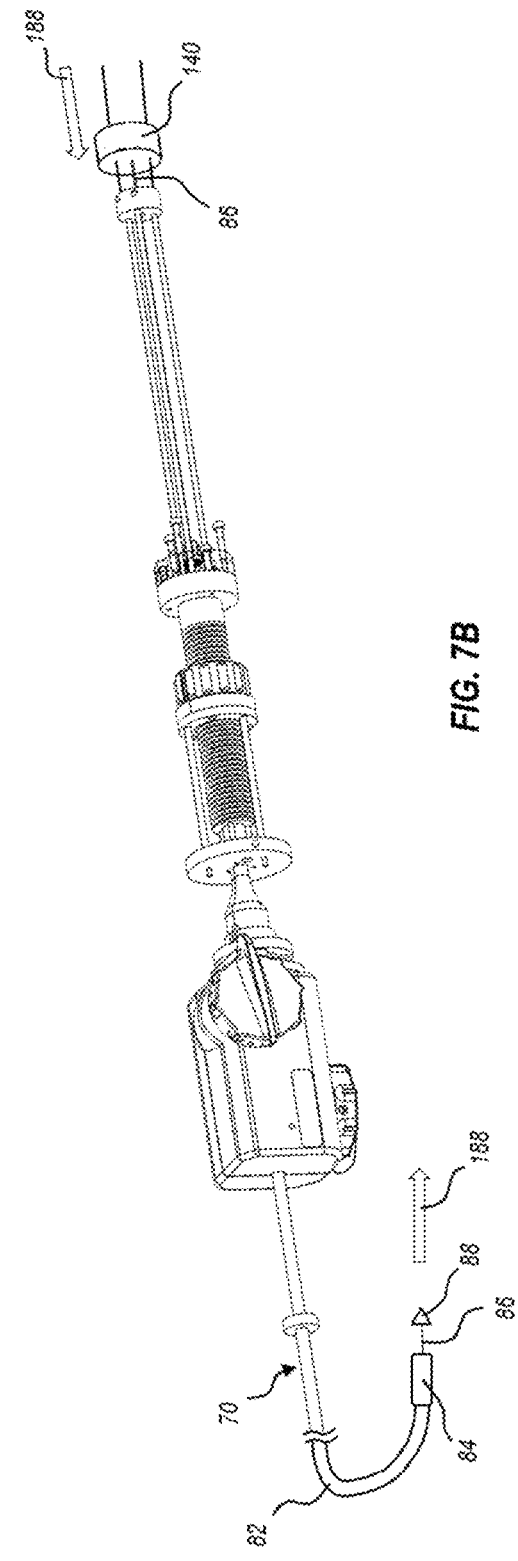

FIGS. 7A and 7B illustrate an operation for moving the guidewire tube 86 and guidewire tube holder 140 relative to the other components of the delivery member 70. FIG. 7A shows, by arrows 187, retraction of the guidewire tube holder 140 and corresponding retraction of the distal tip 88. FIG. 7B shows, by arrows 188 advancement of the guidewire tube holder 140 and corresponding advancement of the distal tip 88. The ability to adjust the distal tip 88 can lower the risk that the distal tip 88 undesirably interferes with chordae tendineae or other cardiac anatomy during deployment procedures. For example, during deployment of an interventional device, the suture catheter 72 may be advanced to disengage from the interventional device. If the distal tip 88 is not retracted relative to the advancing suture catheter 72, the distal tip 88 could extend too far into the ventricle where it could catch chordae tendineae and/or impinge against the cardiac wall.

Elongated Delivery Member Components

Figure 8:
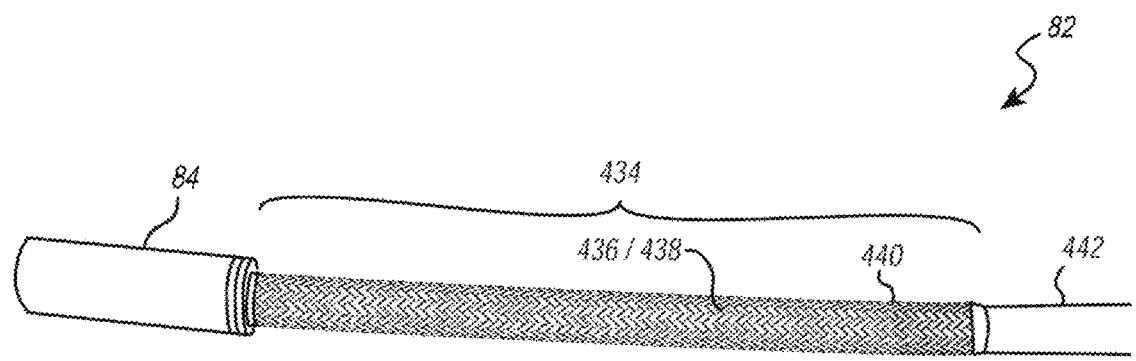
FIG. 8 illustrates the outer sheath, showing various sections that may be formed in the outer sheath.
Figure 9:
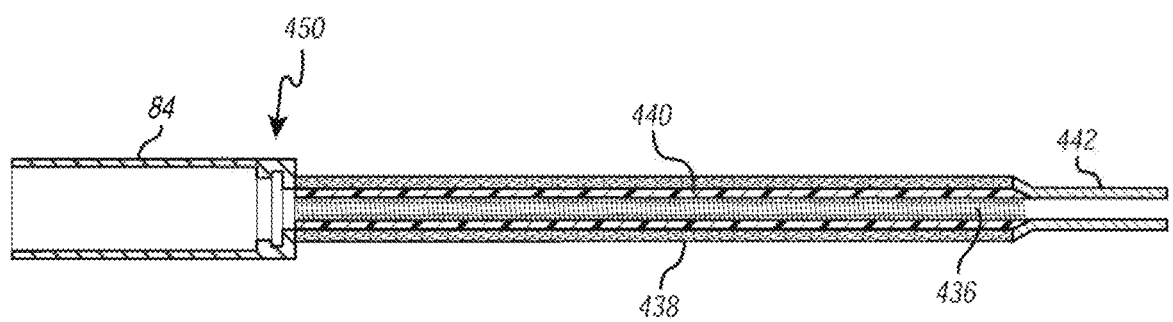
FIG. 9 is a cross-sectional view of the outer sheath of FIG. 8.
Figure 10:
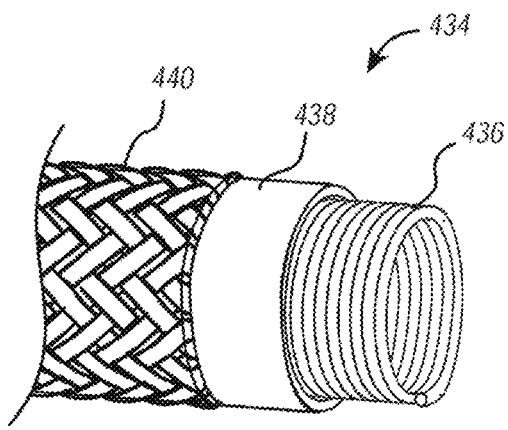
FIG. 10 is a partial cut-away view of an intermediate portion of the outer sheath.

FIGS. 8 and 9 illustrate a portion of the distal end of the outer sheath 82 and distal piece 84 (also occasionally referred to herein as cover 84). Distal piece 84 can be formed as a cylindrical tube having an inner diameter and length sized to receive the interventional device, in a collapsed/pre-deployed configuration, within the lumen of distal piece 84. Distal piece 84 can include a plurality of microfabricated cuts (e.g., laser cuts) and a pair of continuous longitudinal spines located on opposite sides so that distal piece 84 can bend and flex substantially in a single plane. The outer sheath 82 can also include a bending portion 434 that can be attached to and located proximal to distal piece 84. Bending portion 434 may have a sufficient length to surround and extend along that portion of the delivery system that is designed to bend and reorient, via the steerable catheter 80, to navigate through a patient's vasculature and/or heart to a target site for deploying the interventional device. In some embodiments, the bending portion 434 can include a cable tube or coil 436 surrounded by a braided structure 438 (sometimes collectively referred to as the "coil/braid portion 436/438") as shown in FIG. 10.

Attached to the proximal end of bending portion 434 is a cut hypotube 442 that extends from bending portion 434 to the proximal end of the sheath 82. Hypotube 442 can include a plurality of slits and at least one longitudinally continuous spine that can preferably be continuous and uninterrupted along a longitudinal length of, and located at a fixed angular location on, hypotube 442.

In such embodiments, it can be desirable for the bending portion 434 of delivery catheter to remain liquid tight. To seal the bending portion 434, a flexible, fluid impermeable covering can be provided over the coil/braid portion 436/438, extending from the distal piece 84 to a location proximal the coil/braid portion 436/438. For example, the delivery sheath 82 can also include a thin walled flexible cover 440 that extends from the distal piece 84 to the hypotube 442. Flexible cover 440 can be bonded at each end to the underlying structure, using one of a variety of different adhesives, thermal adhesives, UV bonded adhesive, or other techniques.

Additional details and embodiments related to the cover 84/distal piece 84 are described below in the section titled "Interventional device Cover" and are also shown in part by FIG. 18.

Referring again to FIG. 9, outer sheath 82 can also be coupled to distal piece 84 via a swivel connection, generally indicated at 450. To overcome the challenging forces that can develop during insertion of a relatively large delivery catheter into the vasculature of a patient, swivel connection 450 allows rotation of outer sheath 82 by a few degrees, back and forth (i.e., alternating between clockwise rotation and counter-clockwise rotation) while at the same time moving the delivery system 400 in a generally longitudinal direction. This rotational motion (during simultaneous longitudinal translation) helps to overcome some of the longitudinal forces that may resist insertion of outer sheath 82 through a patient's vasculature or frictional forces between the outer sheath 82 and the steering catheter 80.

Figure 11:
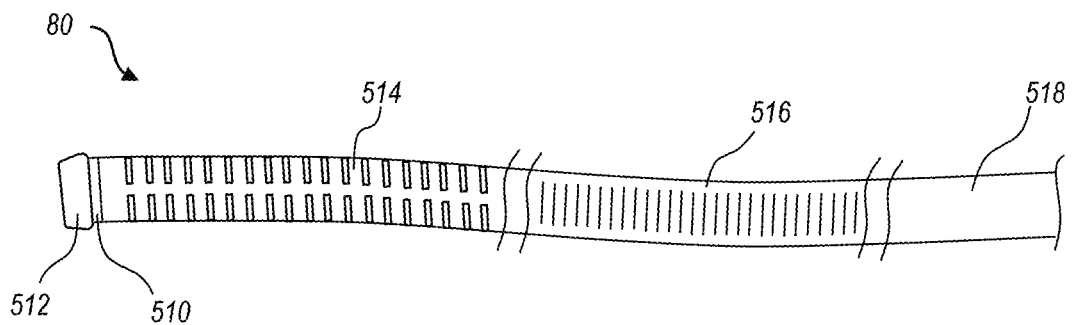
FIG. 11 illustrates the steering catheter, showing various features and sections that may be formed in the steering catheter.

FIG. 11 illustrates one embodiment of the steering catheter 80 in greater detail. In the illustrated embodiments, the steering catheter 80 includes a proximal section 518, intermediate section 516, and a distal section 514. A steering ring 510 (also referred to herein as a tip ring) is connected at the distal end. The one or more tension cables, described above, may extend through the steering catheter 80 and engage with or attach to the steering ring 510 to provide manipulation and control of the curvature of the steering catheter 80. A distal cap 512 positioned over the steering ring 510 or integrally formed with the steering ring 510 provides an angled/rounded surface that allows the steering catheter 80 to more effectively move and slide against the outer sheath 82 without binding. In this embodiment, the steering catheter 80 is formed as a hypotube, such as a laser cut hypotube. The proximal section 518 may remain uncut, while the intermediate section 516 and distal section 514 may be cut (e.g., laser cut) to increase flexibility. Although not shown in this view, a polymer layer may surround the steering catheter and forms an outer layer.

Additional details and embodiments related to the steering ring 510 and/or distal cap 512 are described below in the section titled "Steering Catheter Tip Ring" and are also shown in part by FIGS. 19A and 19B.

In some embodiments, the steering catheter 80 is rotationally keyed to the outer sheath 82. The outer sheath 82 may include cut patterns and/or other features which are arranged to provide particular preferred bending directions. In this embodiment, because bending of the outer sheath 82 depends upon curving of the steering catheter 80, rotational alignment of the outer sheath 82 to the steering catheter 80 is beneficial. These components may be keyed together using a key and corresponding keyway feature, slots and corresponding tabs, or other rotational keying mechanism known in the art. Alternatively, or additionally, alignment markers can be provided at the handle assembly to visually indicate alignment.

To provide effective steering and positioning at the mitral annulus, the distal section 514 is cut with a pattern which allows a bending radius of about 15 mm or less (e.g., 5 to 15 mm). The intermediate section 516 is cut to allow a bending radius of about 30 to 45 cm. The proximal section is uncut to provide the steering catheter 80 with sufficient stiffness, torquability, and pushability.

Figure 12:
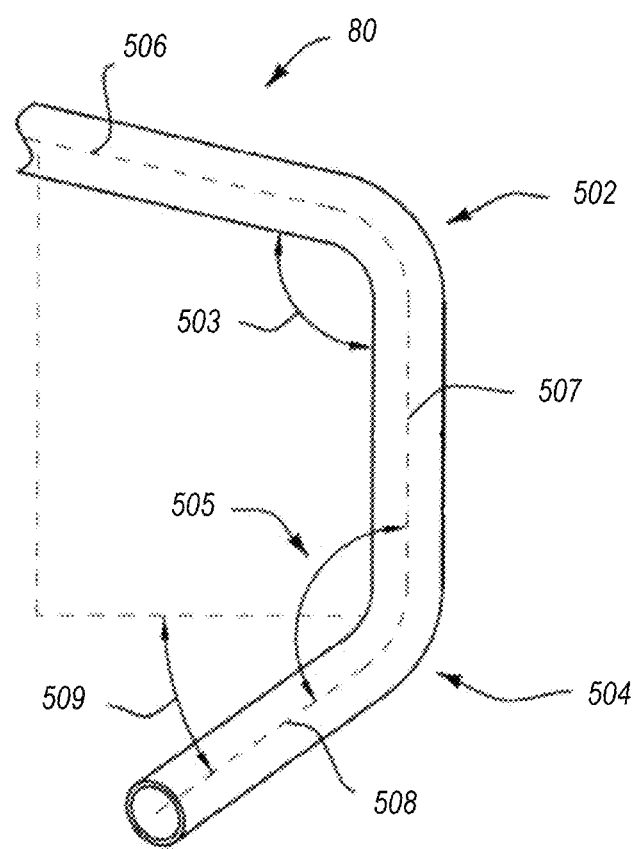
FIG. 12 illustrates the steering catheter after forming a compound curve shape to enable proper positioning of the delivery member relative to the mitral annulus.

FIG. 12 illustrates an example of a series of compound bends that the steering catheter 80 may perform during the delivery, repair, recapture, or repositioning of the interventional device. While accessing the mitral annulus, the steering catheter 80 may be steered in at least two planes of motion. The two planes of motion may be substantially perpendicular to one another. The steering catheter 80 has a first bend 502 with a first bend angle 503 measured between a first longitudinal axis 506 and a second longitudinal axis 507. In some embodiments, the first bend angle 503 may be in a range of about 40° to about 120°, more often about 90° to about 120°, or about 105°. A second bend 504 is formed between a third longitudinal axis 508 and the second longitudinal axis 507. The second bend 504 may also have a rotational angle 509 relative to a plane in which the first longitudinal axis 506 and the second longitudinal axis 507 lie. In other words, the rotational angle 509 is relative to the amount of rotation of the third longitudinal axis 508 relative to the direction of the first bend 502. In one embodiment, the second bend angle 505 is in a range of about 45° to 135° or about 60°.

Figure 13A:
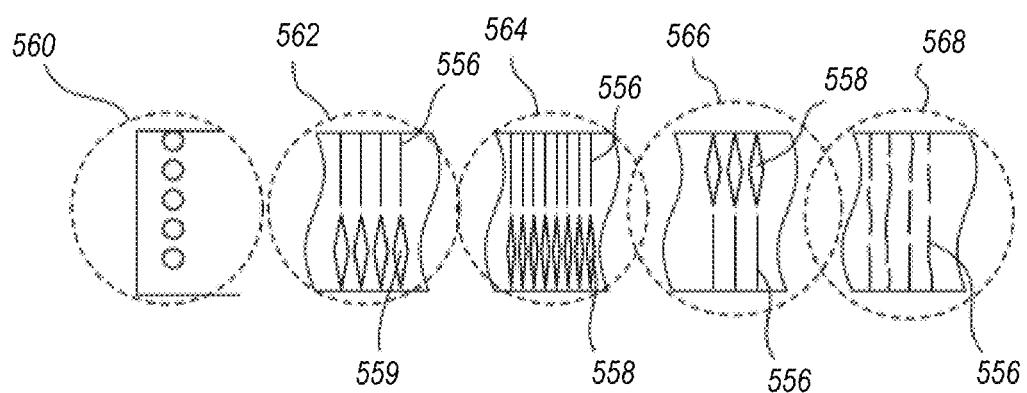
FIG. 13A illustrates various cut patterns which may be utilized in the outer sheath, steering catheter, or delivery catheter, including the can structure, to provide flexibility and/or preferential bending.
Figure 13B:
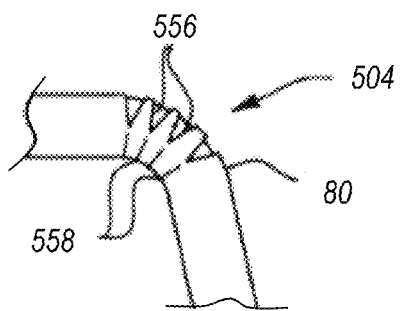
FIG. 13B illustrates bending of the steering catheter, showing features of the cut patterns which enable the bending.

FIG. 13A shows various cutting patterns that can be used in different sections of the steering catheter 80 (and corresponding sections of the outer sheath 82) to produce the desired bends. Each section can include cut patterns that can include one or more slits 556 and/or one or more island cuts 558. The slits 556 may transmit longitudinal force along the catheter and also allow expansion of the catheter when it is deflected in a direction opposite the slit 556. The island cuts 558 may allow compression of the catheter when it is deflected in a direction of the island cuts 558. For example, slits 556 and island cuts 558, when located on opposite sides from one another, may direct preferential bending of the catheter, as shown by exemplary bend 504 in FIG. 13B.

In one embodiment, illustrated in FIG. 13A, a cutting pattern can include five sections or regions 560, 562, 564, 566 and 568, with different cut patterns in each section. Such sections may be arranged as needed to provide the desired compound curve profile. For example, a first section 560 can include a plurality of holes radially spaced about the periphery of the catheter. A second section 562 provides for bending in a first direction, a third section 564 is similar to the second section 562 but with smaller sized and more closely spaced island cuts 558, a fourth section 564 provides for bending in a second direction, and a fifth section 566 includes multiple slits for adding flexibility without forming a particular bending direction. While the island cuts 558 are depicted as diamond-shaped, the island cuts 558 may have one or more other shapes, such as square, rhombohedral, triangular, rectangular, circular, oblong, other elliptical, other polygonal, irregular, or combinations thereof.

Additional details and embodiments related to the steering catheter 80, including additional and/or alternative cut patterns that may be utilized in the steering catheter 80, are described below in the section titled "Gradient Cut Pattern" and are also shown in part by FIG. 19C.

Figure 14:
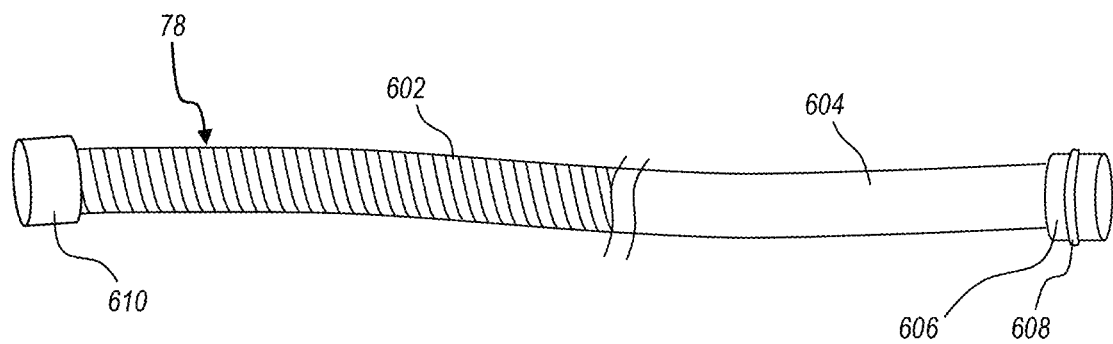
FIG. 14 illustrates a delivery catheter with distal cap structure configured for maintaining at least a portion of the interventional device in a compressed configuration pre-deployment.

FIG. 14 illustrates one embodiment of the delivery catheter 78. The delivery catheter 78 includes a proximal section 604 and a distal section 602. At the proximal end, the delivery catheter 78 may include a seal 606 and an O-ring 608 for forming a fluid tight seal at the handle assembly 130, in particular at the delivery catheter holder 136. In the illustrated embodiment, the distal section 602 is formed as a coil. The coil provides the delivery catheter 78 with ability to effectively push the valve device through the steering catheter 80 as part of deploying the valve device. The coil also provides good flexibility for navigating a patient's tortuous vasculature.

The delivery catheter 78 also includes a can structure 610 disposed at the distal end. The can 610 is configured to constrain and hold at least a proximal section of a collapsible/expandable interventional device 10. Without such constraint, the outer portion of the device 10 may bias radially outward against the inner surface of the overlying components of the delivery member 70, making it more difficult to unsheathe or re-sheathe the device 10. Further, in implementations where the interventional device 10 includes hooks or barbs, the can 610 can aid in isolating the hooks/barbs and preventing them from catching onto cuts or other areas of the delivery member 70.

The can 610 may also have a length sufficient to aid in maintaining coaxial alignment of the distal end of the delivery catheter 78 within the delivery member 70 to avoid or minimize unwanted tilting. For example, the can 610 preferably has a length to diameter ratio of greater than or equal to 1, though in alternative embodiments the ratio may be smaller, such as about 0.25 to 1, depending on the stiffness of the distal section 602. The can 610 also provides an effective structural surface to act as a counterforce to maintain the interventional device 10 in the proper pre-deployed position when the outer member is retracted. In some embodiments, one or more edge portions of the can 610 include a taper and/or smooth surface for easier sliding of the can 610 within the outer member.

Additional details and embodiments related to the delivery catheter 78, including additional and/or alternative can structure embodiments and additional or alternative structures for forming the structure of the catheter 78, are described below in the section titled "Additional Features of the Delivery Catheter" and are also shown in part by FIGS. 20A and 20B.

Figure 15:
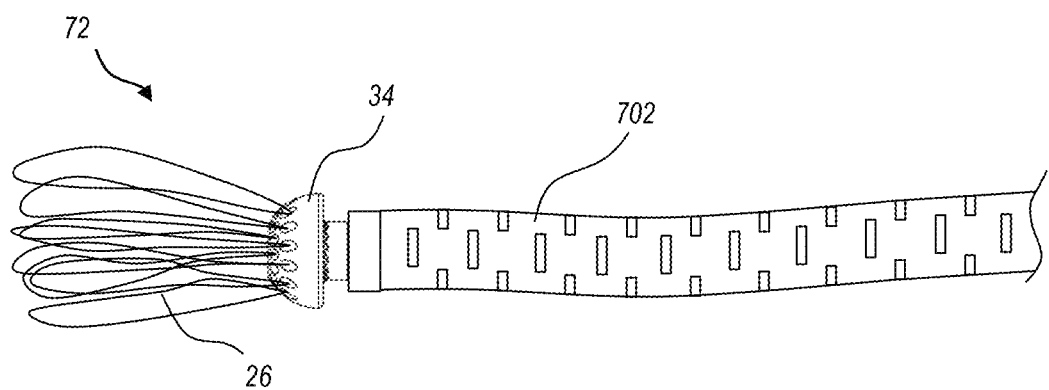
FIG. 15 illustrates an exemplary suture catheter that may be disposed within the delivery catheter of FIG. 14 and which is configured for controlling axial tension on the replacement heart valve.

FIG. 15 is a detail view of the inner catheter 72 (which may also be referred to herein as a "suture catheter"). The inner catheter 72 may be utilized as part of the delivery member 70 to maintain axial tension of the interventional device prior to deployment, and by so doing may aid in maintaining at least the proximal section of the interventional device within the can 610. For example, the inner catheter 72 may include a connecting ring 34 with a series of suture loops 26 that may be tethered to corresponding attachment points of the interventional device (see further details in FIGS. 16A through 16F). Retraction of the inner catheter 72 relative to the delivery catheter 78 adds axial tension to the interventional device to maintain it in a pre-deployed position while distal movement of the inner catheter 72 relative to the delivery catheter 78 releases axial tension and allows deployment of the device.

Additional details and embodiments related to the inner (suture) catheter 72, including details regarding a coil component that may be included with the inner catheter 72, are provided below in the section titled "Coil Component for Suture Catheter" and are also shown in part in FIG. 21.

Deployment of the Interventional Device

Figure 16A:
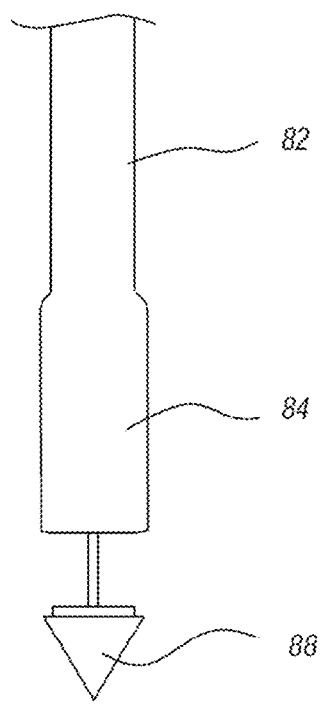
FIGS. 16A through 16F illustrate deployment and release of the replacement heart valve at the mitral annulus.
Figure 16B:
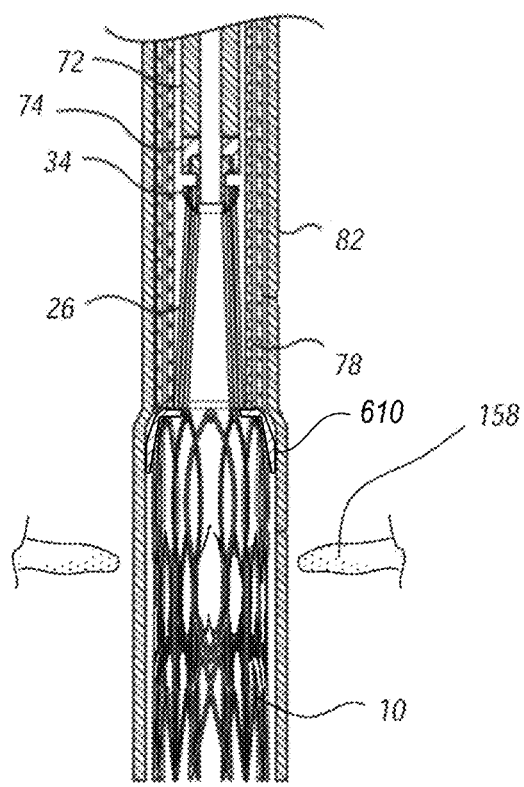
Figure 16C:
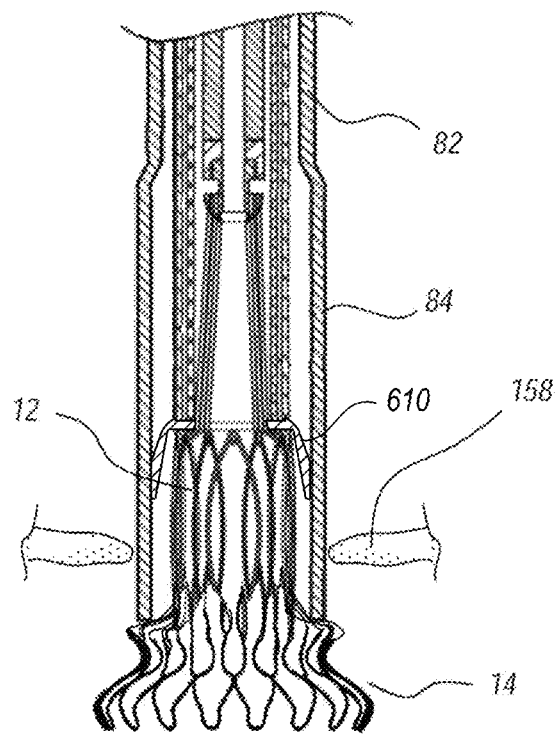
Figure 16D:
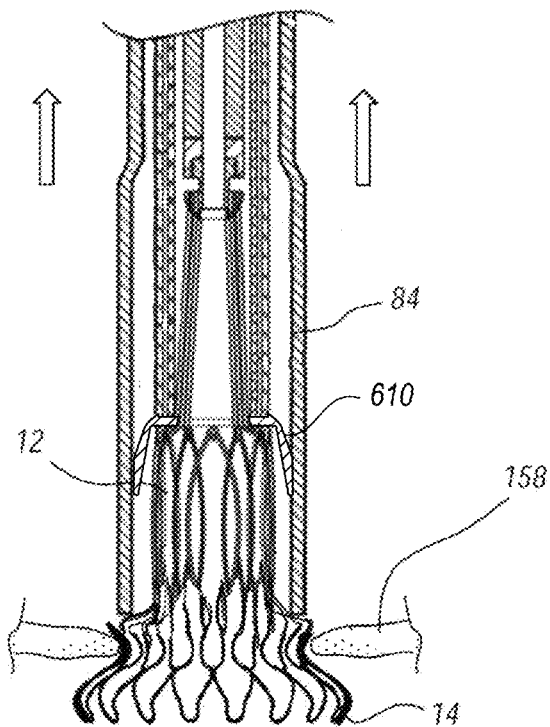

FIGS. 16A through 16F schematically illustrate deployment and release of an interventional device 10 (shown here as a replacement valve) at the mitral annulus 158. As shown in FIG. 16A, the distal tip 88 is first advanced relative to the outer sheath 82 and valve cover 84 to provide sufficient space for deployment. For clarity, in following Figures, the tip 88 is not shown. FIG. 16B shows in cross-section the delivery member in position at the mitral annulus 158, with a distal portion of the valve 10 positioned on the ventricular side, and a proximal portion of the valve 10 positioned on the atrial side. Partial retraction of the outer sheath 82, as shown in FIG. 16C, allows the ventricular anchor 14 to release and expand. As shown in FIG. 16D, the valve 10 may then be retracted proximally to bring the ventricular anchor 14 into contract against the mitral annulus 158. This may be accomplished by retracting the delivery catheter 78. Alternatively, the entire delivery member 70 may be retracted.

Figure 16E:
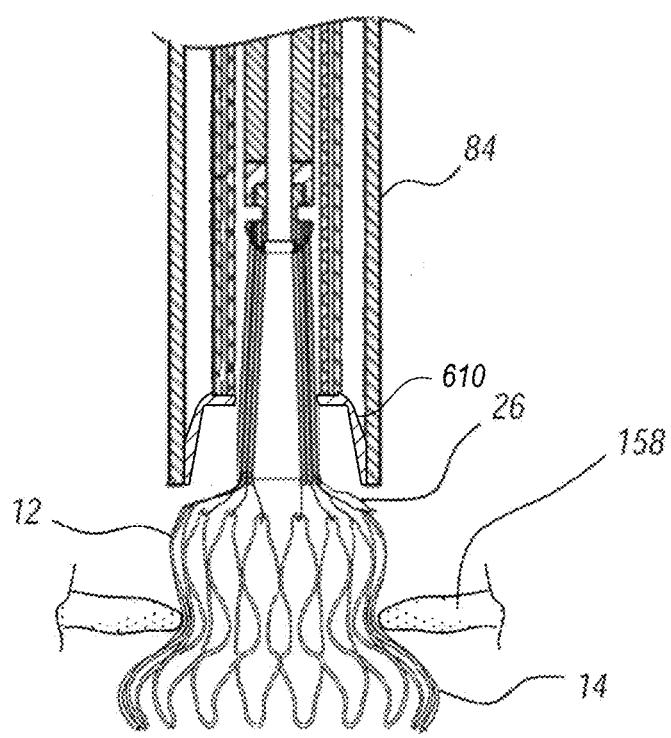
Figure 16F:
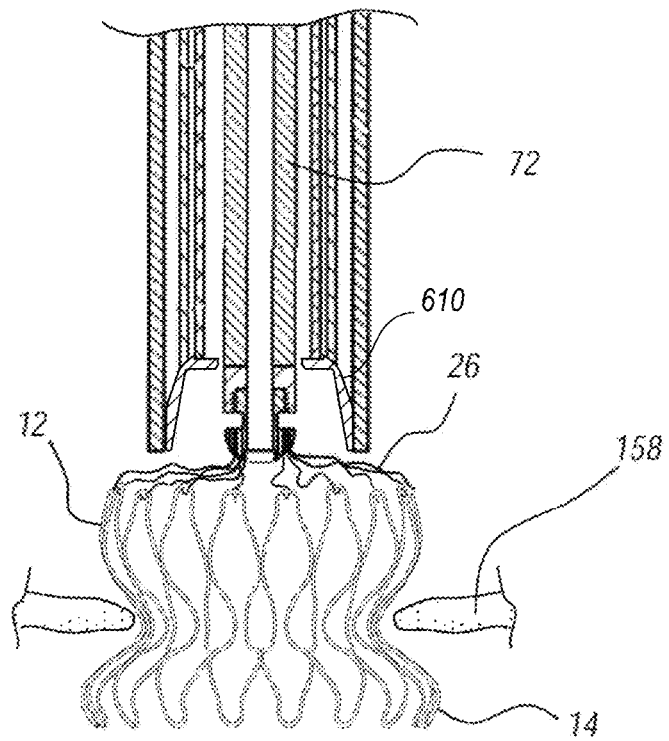

As shown by FIG. 16E, the valve cover 84 may then be further retracted to release the atrial anchor 12 on the atrial side of the mitral annulus 158. At this point, the valve 10 may still held by the suture loops 26 in a position not yet fully deployed. This allows the valve 10 to be further positioned or recaptured if necessary. As shown in FIG. 16F, the suture catheter 72 may then be distally advanced to relieve tension in the suture loops 26, allowing the atrial anchor 12 to more fully expand and release from the can structure. Even further distal advancement of the delivery catheter detaches the suture loops 26 and allows the delivery member 70 to be removed from the patient. The longitudinal position of the tip 88 relative to the suture catheter 72 can be adjusted as needed while the suture catheter 72 is advanced. After the valve 10 is detached, the tip 88 is retracted and reconnected to the valve cover 84 prior to removal of the delivery member from the patient.

Quick-Release Control for Suture Catheter

In the embodiment shown in FIGS. 6A and 6B, the suture catheter control 139 is threadedly engaged with the suture catheter holder 138 such that advancement or retraction of the suture catheter relative to the delivery catheter is controlled by rotation of the suture catheter control 139. While this configuration allows for finely controlled adjustments of the suture catheter position relative to the delivery catheter, there are several circumstances where an alternative suture catheter control would be beneficial.

For example, positioning of an interventional device, such as a replacement valve, in the mitral annulus includes certain steps where the timing of deployment can be important. With reference again to FIG. 16C, after the ventricular anchor 14 has been released and allowed to expand on the ventricular side of the annulus 158, there will typically be some space, initially, between the ventricular anchor 14 and the annulus 158. This space typically allows the natural leaflets of the heart valve to continue to function, which allows blood to continue to flow around and/or through the replacement valve 10 from the left atrium into the left ventricle 159 (FIG. 3).

However, in a following step, the delivery system may be pulled back proximally to seat the ventricular anchor 14 against the ventricular side of the annulus 158 (see FIG. 16D) in preparation for deployment of the atrial anchor 12. With the ventricular anchor 14 seated against the annulus 158, the function of the natural valve leaflets will be impeded, but the artificial replacement valve 10 will not yet have been deployed in a functional state, thus little or no blood will be able to flow between the left atrium and left ventricle. It is therefore beneficial for the delivery system to be able to rapidly deploy the atrial anchor 12 following seating of the ventricular anchor 14 against the annulus 158 in order to quickly restore the blood flow between the left atrium and left ventricle.

As described above, the atrial anchor 12 is deployed when the suture catheter 72 is advanced distally relative to the delivery member 70. This is accomplished in the above embodiment by rotating the suture catheter control 139 to move the suture catheter holder 138. The threaded engagement of these components, however, does not allow for rapid distal movement of the suture catheter holder 138.

Figure 17A:
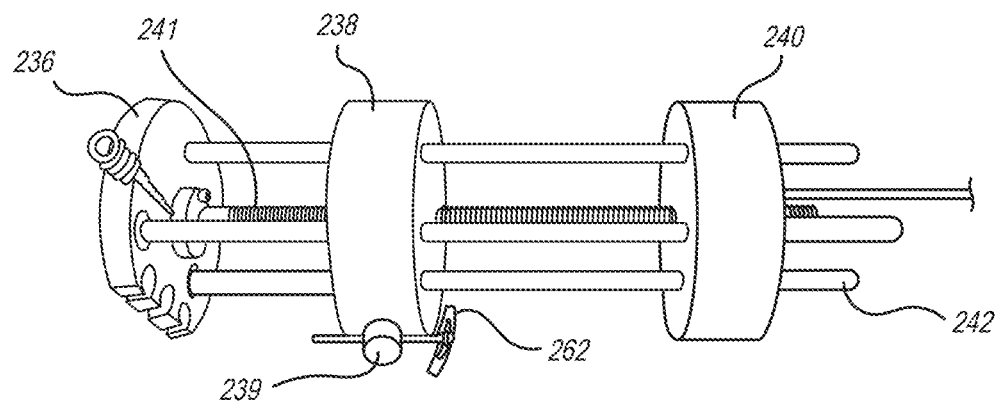
FIGS. 17A and 17B illustrate of a suture catheter control mechanism that may be utilized to provide rapid actuation and translation of a suture catheter holder relative to a delivery catheter holder.
Figure 17B:
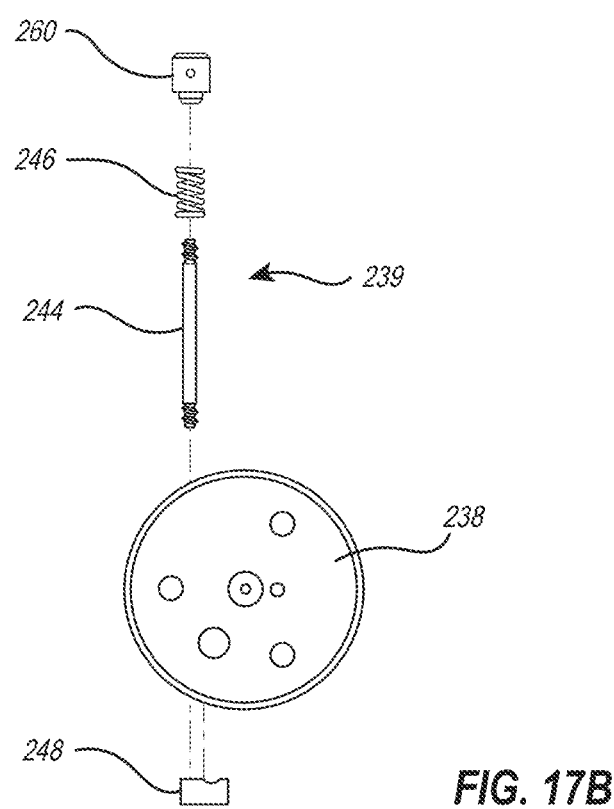

FIGS. 17A and 17B illustrate an alternative embodiment of a suture catheter control mechanism that may be included as part of the handle assembly and that may be utilized to provide rapid actuation and translation of a suture catheter holder 238 (also referred to herein as an inner catheter holder 238) relative to a delivery catheter holder 236. The illustrated embodiment is beneficially capable of rapidly causing release of the atrial anchor 12 and thereby capable of rapidly restoring blood flow through the replacement valve 10 between the left atrium and left ventricle.

In the illustrated suture catheter control mechanism, a proximal section of the suture catheter 72 is connected to the suture catheter holder 238, which may be formed as a slidable "puck" or other structure readily manipulatable by a user. Although puck-like structures 236, 238, 240 are shown in the illustrated embodiment, other embodiments may utilize other shapes, including spheres, ovoids, polygons, and/or shapes having handles, for example.

A proximal section of the delivery catheter 78 is connected to the delivery catheter holder 236 such that the suture catheter 72 can extend from the suture catheter holder 238 and enter the delivery catheter 78 at the delivery catheter holder 236. A guidewire tube holder 240 may also be disposed on the actuation mechanism and supported by the alignment rods 242. A proximal section of the guidewire tube 86 may be coupled to the guidewire tube holder 240, and may extend from the guidewire tube holder 240 so as to enter the suture catheter 72 at the suture catheter holder 238.

One or more alignment rods 242 may extend from the delivery catheter holder 236 to support the suture catheter holder 238 and the guidewire tube holder 240. The suture catheter holder 238 and the guidewire tube holder 240 are selectively coupled to a lead rod 241, which forms a mechanical linkage that couples the delivery catheter holder 236 and suture catheter holder 238 together. When the suture catheter holder 238 and the guidewire tube holder 240 are coupled to the lead rod 241, their longitudinal positions are fixed relative to the delivery catheter handle 236, allowing the delivery catheter 78, suture catheter 72, and guidewire tube 86 to be moved together relative to one or more other components of the delivery member 70. Conversely, when the suture catheter holder 238 and/or the guidewire tube holder 240 are uncoupled from the lead rod 241, one or both may be moved longitudinally relative to the delivery catheter handle 236.

As discussed above, longitudinal movement of the suture catheter holder 238 relative to the delivery catheter holder 236 causes longitudinal movement of the suture catheter 72 relative to the delivery catheter 78. Because the suture catheter holder 238 is configured to readily slide along the alignment rods 242, it may be rapidly and selectively moved. This may be beneficial, for example, for rapidly actuating an atrial anchor 12 of a replacement valve 10, as discussed above. Similarly, longitudinal movement of the guidewire tube holder 240 causes longitudinal movement of the guidewire tube 86 relative to the other components of the delivery system.

The suture catheter holder 238 and/or guidewire tube holder 240 may include a release mechanism 239 allowing each component to be selectively coupled to and released from the lead rod 241. An example is shown here as part of the suture catheter handle 238. As shown in the exploded view of FIG. 17B, the release mechanism 239 may include a pin 244 biased by a spring 246. An end piece 248 may also be attached to the end of the pin 244 opposite a cap 260.

When the release mechanism 239 is depressed or otherwise selectively actuated, the pin 244 and end piece 248 are disengaged from the lead rod 241, and the suture catheter holder 238 is free to slide along the alignment rods 242. When the release mechanism is released, the release mechanism 239 biases back against the lead rod 241 to re-engage and relock the longitudinal position of the suture catheter holder 238. As shown, the lead rod 241 may be threaded and/or include other structures (grooves, divots, depressions, etc.) for engaging with the release mechanism 239 when in the engaged position. Although a spring-loaded pin such as shown has been found to provide effective and rapid actuation, other engagement mechanisms may additionally or alternatively be utilized, such as a toggle release, snap shackle, quick-release skewer, and/or set screw, for example.

To avoid an unintended movement of the suture catheter 72, the release mechanism 239 may also include a safety pin 262 positioned to prevent inadvertent depression/activation of the release mechanism 239. The safety pin 262 may be positioned transversely through the cap 260 of the release mechanism 239, for example.

To release the atrial anchor 12 and unhook the sutures from the replacement valve 10 using the illustrated suture catheter control mechanism, the safety pin 262 is removed, release mechanism 239 is actuated, and the suture catheter holder 238 is slid along the alignment rods 242 toward to the delivery catheter holder 236. The separation between the suture catheter holder 238 (in its pre-deployed position) and the delivery catheter holder 236 can provide a predetermined, metered distance needed to move the suture catheter 72 distally a distance sufficient to reliably cause the suture loops to disengage from the atrial anchor 12 of the artificial valve 10. In this way, the suture loops will slide forward and will at the final distal position invert to ensure that they will slide off the hooks of the valve 10.

After fully deploying the replacement valve 10 and released from the delivery system, the suture catheter 72 may be retracted back within the delivery member 70 by actuating the release mechanism 239 and pulling the suture catheter handle 238 proximally away from the delivery catheter handle 236. This will pull the suture loops back into the delivery member. The guidewire tube handle 240 may then be actuated and moved to adjust the position of the distal tip 88 in preparation for retracting the entire delivery member 70 from the patient's vasculature.

Interventional Device Cover

Figure 18:
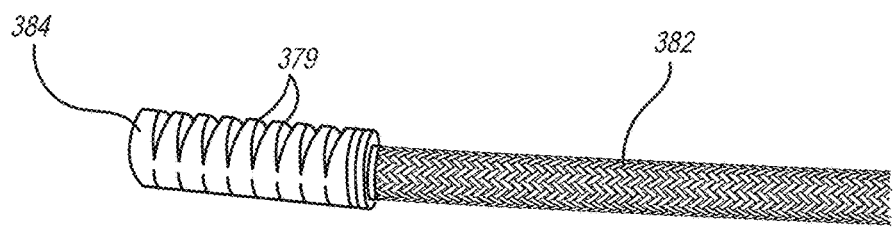
FIG. 18 illustrates an embodiment of an outer sheath and attached cover, the cover being configured to house an interventional device intended for delivery to a targeted cardiac region.

FIG. 18 illustrates another embodiment of an outer sheath 382 and attached cover 384 (i.e., distal piece 384) that may be substituted for the cover 84 described above. In preferred embodiments, the cover 384 is formed from a medical grade titanium such as grade 5 titanium. Such an embodiment preferably also includes slits 379 that have been formed with a short pulse laser in order to avoid any re-melt on the internal diameter of the piece. In addition, such an embodiment may include smooth edges around the laser cuts. For example, on a last pass of laser cutting, the beam can be defocused to thereby smooth the edges of the laser cuts.

Forming the cover 384 from titanium is beneficial because the titanium is very hard and will not interact with a nitinol interventional device housed within the cover 384, even if the nitinol were to scratch across its surface. In addition, the use of titanium in the cover 84 limits the risk of contamination of a nitinol interventional device housed therein.

Interventional devices are often made from nitinol. When utilized as implants, these devices may be required to withstand dynamic loads of hundreds of millions of cycles. It is therefore desirable to avoid excess fatigue and contamination. One potential source of contamination can happen when nitinol is brought into contact with a dissimilar metal such as stainless steel. For example, iron from the steel could migrate into the nitinol and negatively influence fatigue life.

In some circumstances, relatively high forces may be required to sheath an interventional device, such as a replacement valve, within the cover 384 and to release the device when it is positioned at the appropriate target. The nitinol frame of the device is therefore likely to scratch against the inner surface of the cover 384. Forming the valve cover from a polymeric material is less preferred since the relatively high forces involved may deform the cover. As noted above, a metal such as stainless steel is also less preferred due to the risk of contamination of the interventional device.

Some embodiments may form the valve cover from stainless steel and then provide a coating to separate the stainless steel from the nitinol of the interventional device housed within the cover. However, these embodiments are also less preferred because some interventional devices include sharp hooks or barbs that may scratch against the inner surface of the cover as the cover is retracted relative to the interventional device which may cause the coating to flake off. Further, it may be difficult to adequately coat the cover, particularly the inner surface of the cover where the interventional device will have the most contact. Even a strong coating such as a diamond coating may be difficult to coat in a manner that will prevent flaking off under loading and release conditions.

Use of titanium in the cover 384, in addition to the benefits mentioned above, also allows for a relatively thin walled component such as in the range of about 0.2 mm to about 0.5 mm, or about 0.3 mm to about 0.4 mm. In one method of manufacturing the cover 384, a thin-walled cover is machined from a solid titanium rod. This allows for a thinner final wall thickness than would be readily achievable by drawing the tube structure, for example.

A thin-walled cover such as within the size ranges described above may also allow for visualization of the underlying interventional device while it is partially housed within the cover 384. For example, the cover 384 may be sufficiently echotransparent to enable echocardiographic visualization of the underlying portions of the interventional device during a procedure.

The proximal terminus of the cover 384 connects to the remainder of the outer sheath 382, which is typically formed from stainless steel. It is possible to directly weld titanium to stainless steel. However, a mechanical connection such as a threaded connection is more preferred.

The proximal portion of the cover 384 may also be able to bend to an angle up to about 75°, or about 90°, in order to be properly oriented superior to the mitral annulus. A cut pattern (e.g., formed via laser cutting) forming slits 379 may therefore be formed in at least the proximal portion of the cover. The cut pattern (such as one or more of the examples shown in FIGS. 13A and/or 19C) may be aligned to provide a preferred bending plane that allows a deflection of at least about 75°, or about 90°.

The cover 384 may be deburred after the cut pattern is formed. Methods using chemical deburring and/or a short pulse laser are less preferred because chemical deburring may not remove all the slag and short pulse laser procedures are slower and more expensive. A mechanical honing process is preferred. The cover 384 is preferably passivated following machining, cutting, and honing. After machining, cutting, deburring and/or honing, the cover can also be coated with an anti-friction and/or anti-wear coating as are known in the art.

Steering Catheter Tip Ring

Figure 19A:
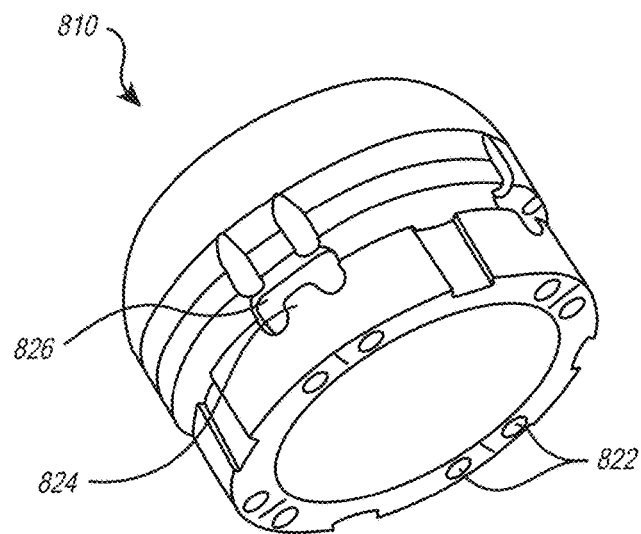
FIGS. 19A and 19B illustrate an embodiment of a tip ring that may be utilized at the distal end of the steering catheter.
Figure 19B:
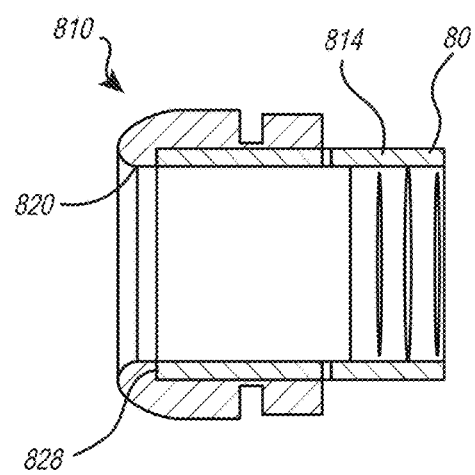

FIGS. 19A and 19B illustrate an embodiment of a tip ring 810 that may be utilized at the distal end of the steering catheter 80 (e.g., in place of the steering ring 510 and distal cap 512 described above).

To minimize the interactions between the steering catheter 80 and the delivery catheter 78, it is beneficial to omit sharp edges at the distal end of the steering catheter 80, especially on the inner surfaces at or near the distal end of the steering catheter. As best shown in the cross-sectional view of FIG. 19B, for example, the tip ring 810 may include a rounded distal edge surface 820 that prevents binding against components intended to translate within the steering catheter 80, such as the delivery catheter 78.

As described above, the steering catheter 80 may include one or more lumens for holding one or more corresponding tension cables for controlling the curvature of the steering catheter 80 at various positions. The tip ring 810 includes corresponding lumens 822 through which the tension cables may be routed. The tip ring 810 may also include one or more seats 824 and corresponding cutouts 826. The seats 824 provide a surface upon which a tension cable can pass over before being routed back toward the steering catheter 80. The seat 824 therefore limits the radius of curvature of the tension cable at that turning point, and may be configured to reduce the risk of pinching and damaging the tension cable. The tip ring 810 also allows the tension cable(s) to be engaged by routing them through a lumen 822, over the seat 824, and back down another adjacent lumen 822, which beneficially reduces the need to rely solely on welding or adhesives to attach the tension cables to the tip ring 810.

Since the tension cables essentially only transmit pull force, the steering ring 810 will be pulled back during steering manipulations. This can put a lot of stress on the joint between the tip ring 810 and the distal portion 814 of the steering catheter 80. To provide a stable joint sufficient for supporting these stresses, the tip ring 810 may include a step 828 that forms an inner diameter on the proximal side of the ring 810 having substantially similar dimensions as the distal section 814 of the steering catheter 80. The distal section 814 can be inserted into the resulting pocket, thereby forming a smooth transition between the steering catheter 80 and the tip ring 810.

With the distal end 814 of the steering catheter 80 inserted in the pocket formed in the proximal side of the tip ring 810, the tip ring 810 can be laser welded to the distal end 814 with a laser seam weld. The laser weld can be a continuous line on the coincident inner diameter portion connecting the distal section 814 and the tip ring 810. A continuous seam weld can beneficially smooth out potential tolerance mismatches between the inner diameter of the tip ring 810 and the inner diameter of the distal section 814.

Gradient Bend Cut Pattern

Figure 19C:
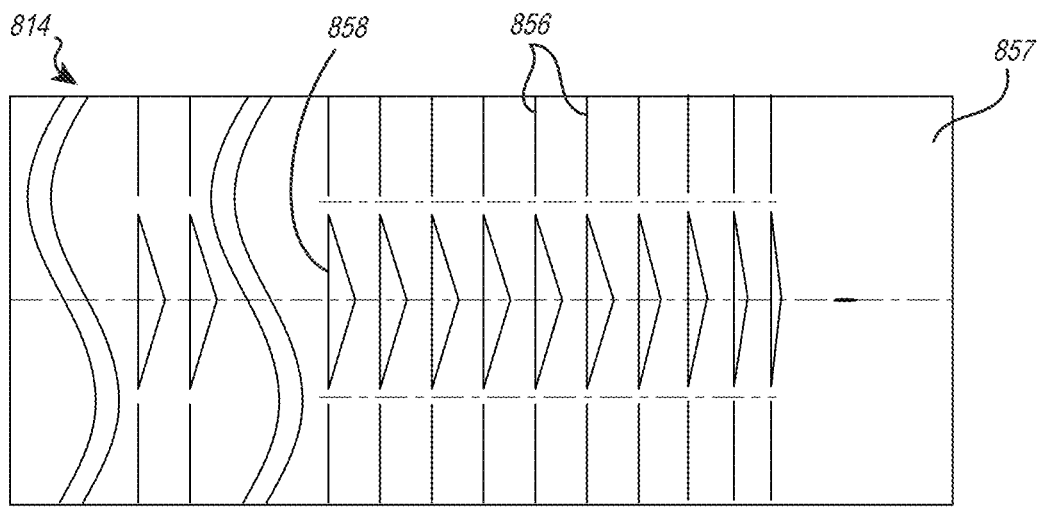
FIG. 19C illustrates an embodiment of a cut pattern that may be utilized in at least a portion of the suture catheter and/or in other components of the delivery member to provide a gradient bending profile.

FIG. 19C illustrates another embodiment of a cut pattern that may be utilized in a steering catheter 80 and/or other components of the delivery member 70 to allow for a desired flexibility and curve profile. The cut pattern embodiment shown in FIG. 19C may be combined with one or more of the cut pattern embodiments described above and shown by FIG. 13A, for example. The cut pattern shown in FIG. 19C illustrates an exemplary distal section 814 of the steering catheter 80 as if cut along a longitudinal line and unrolled to lay flat.

As with some of the cut patterns described above, the illustrated cut pattern may include a plurality of slits 856 and island cuts 858. The slits 856 and island cuts 858, when disposed on opposite sides from one another, may define a preferential bending direction of the catheter (see FIG. 13B) along a neutral axis defined by the two spines 857 formed between the slits 856 and island cuts 858 (which are circumferentially opposite one another when the cut pattern is "rolled up"). As shown, the island cuts 858 may be formed so that they progressively change in size in along the length of the cut pattern. For example, the island cuts 858 may progressively get smaller along the length of the cut pattern in the distal direction. Such a cut pattern would provide a gradient bend that gradually increases in deflection at successively more proximal sections.

One of the functions of the delivery system described herein is to position the distal tip into the mitral annulus so that an interventional device (e.g., replacement valve 10) may be deployed in the proper location. This may be accomplished by bending the steering catheter in two separate planes (e.g., via a transseptal approach). To reduce unwanted interaction and/or binding between various components of the delivery member, it is desirable that sharp bends near the distal end are avoided.

The distal-most section of the steering catheter preferably has a relatively straight section. In the illustrated cut pattern, this may be manifest as an uncut section 857. The uncut, relatively straight portion allows the components advancing past the distal end of the steering catheter 80 to continue along a straight path. For example, by pointing the distal end of the steering catheter directly at the mitral annulus, the components advancing distally beyond the steering catheter 80 (e.g., the delivery catheter 78) will continue on a straight trajectory toward/through the annulus. Moving proximally from the straight, uncut section 857, the bend in the steering catheter forms gradually before increasing to form the full bend.

Additional Features of the Delivery Catheter

As described above, the delivery catheter 78 may have to withstand relatively high compression forces during deployment of an interventional device. For example, during release of a replacement valve 10 by retraction of the outer sheath 82, the countervailing compression force on the delivery catheter 78 may be on the order of about 100 lbs. The delivery catheter 78 must also have sufficient flexibility to allow for proper deflection and curvature to obtain the desired position at the mitral annulus.

A coil structure, such as in the distal section 602 of the delivery catheter 78 as shown in FIG. 14, is beneficial because it has high flexibility and is also able to withstand high compression forces. In some embodiments, the coil may be a flat wire coil. A flat wire coil has been found to provide effective balance between flexibility and compressive strength.

Although the use of a coil in the delivery catheter 78 is beneficial, when the coil is passed into a bend it forms open gaps at the outer side of the curve. The open gaps in the curved part of the coil can make it more difficult to advance and retract the delivery catheter 78 through an outer member (e.g., the steering catheter 80 and/or outer sheath 82). In particular, the gaps of the coil may tend to interact with the laser cut structures of the steering catheter 80 and/or the distal edge of the outer member.

In some embodiments, friction could be lowered by using coatings such as silicon oil. However, it has been found that in some instances, even where a thick coating is used, the delivery catheter 78 may still move in a "stuttering" manner because gaps in the coil interact with the inner surfaces of the outer member. The tighter the deflection in the outer member, the worse this stuttering phenomenon may be during advancement/retraction of the delivery catheter 78.

Other embodiments may include a covering disposed over the coil of the delivery catheter 78. The cover may include a shrink tube such as a PTFE shrink tube, for example. However, such coverings have been found to bunch/fold on the inner side of curves formed in the delivery catheter 78. In some circumstances, this undesirably reduces the overall flexibility of the coil.

Figure 20A:
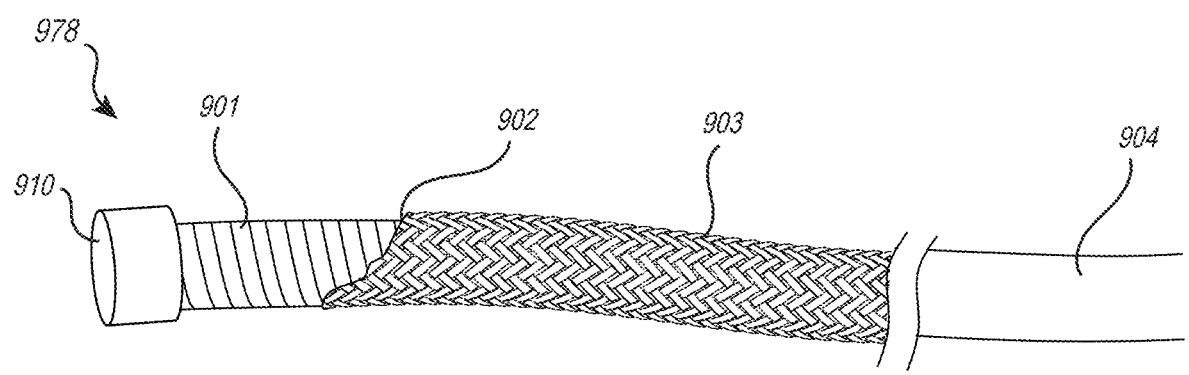
FIG. 20A illustrates an embodiment of a delivery catheter having a distal section formed as a coil/braid composite.

FIG. 20A illustrates a preferred embodiment of a delivery catheter 978 having a coil section 901 and a braid section 903 coupled to the coil (e.g., via soldering). The braid section 903 may be coupled to the coil section 901 with sufficient looseness/slack to allow the coil/braid composite to bend from about 0° to about 180°, at least about 180° to about 540°, more preferably about 270° to about 360°. Too little slack tends to cause the braid section 903 to become fully stretched too soon, preventing further bending of the underlying coil section 901. On the other hand, too much slack may cause the braid section 903 to bunch/bulge when retracted through the distal end of the steering catheter 80.

The coil/braid composite may form a distal section 902 of the delivery catheter 978, while a proximal section 904 is formed of a hypotube. The hypotube of the proximal section 904 may be cut with a cut pattern as described herein (see, e.g., FIGS. 13A and 19C). The proximal section 904 and distal section 902 may be joined by a weld (e.g., a laser weld). A spacer ring may be added to allow welding on the outside diameter of the hypotube of the proximal section 904 and inside diameter of the coil/braid composite of the distal section 902. This forms a stable joint that avoids welding on the braid or solder section.

Figure 20B:
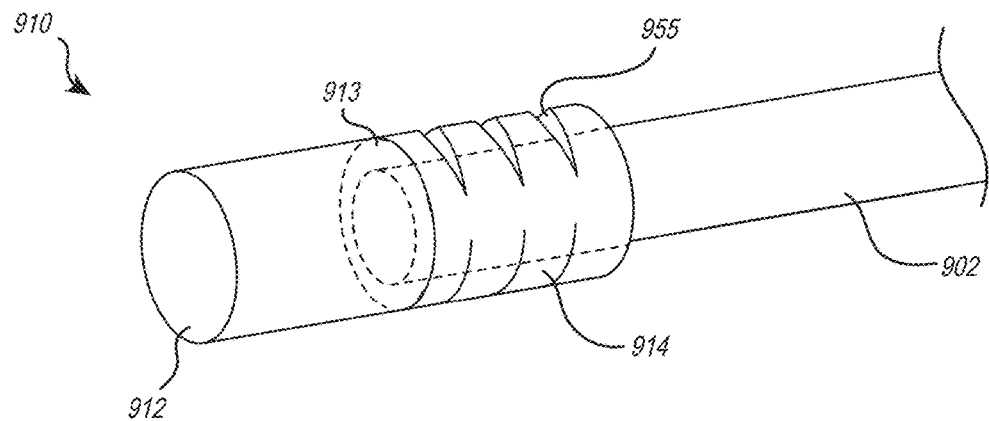
FIG. 20B illustrates an embodiment of a can structure having a cut pattern for providing additional flexibility and having a proximal section extending proximally to provide additional length to the can structure.

As shown, the delivery catheter 978 may also include a can structure 910, which is shown in detailed view in FIG. 20B. The can structure 910 may be configured similarly to the can structure 610 except as noted below. As shown, the can structure 910 may include a cut pattern 955, which may be configured such as any combination of cut patterns shown in FIGS. 13A and 19C.

Providing a cut pattern 955 in the can 910 beneficially enhances the flexibility of the can 910 without detrimentally removing the beneficial structural features of the can 910. For example, the can 910 may be provided with a cut pattern 955 that allows it to flex along with coincident portions of the delivery member 70 (such as the steering catheter 80). In this way, the can 910 does not become an overly stiff/rigid section of the device relative to the other coincident portions of the delivery member 70. In the absence of such a cut pattern, for example, the can 910 may be relatively stiff/rigid and may reduce the ability to effectively navigate and position the device, particularly when the can 910 is passed through a curve in the other components of the delivery member 70.

Including a cut pattern 955 in the can 910 also allows the can 910 to have a greater length. In the absence of cuts, extending the length of the can 910 could create an overly long stiff/rigid section of the delivery member 70. However, with the inclusion of a cut pattern 955 that allows greater flexibility of the can 910, the length of the can 910 may be increased without sacrificing the flexibility of the overall delivery member 70. The can 910, with cut pattern 955, may have a length to diameter ratio of greater than or equal to 1, such as about 1.5, 2, 2.5, 3, 3.5, 4, or within a range with endpoints defined by any two of the foregoing values.

As shown, the can 910 may include a proximal section 914 and a distal section 912 separated by a divider 913. In this embodiment, the proximal section 914 includes the cut pattern 955 while the distal section 912 remains free of cuts. The cut pattern 955 is preferably formed such that the proximal section 914 bends substantially in the same plane and at the same angle as the coincident portions of the delivery member 70 surrounding the proximal section 914.

The divider 913 limits the movement of the interventional device when positioned within the distal section 912 of the can 910. The additional length provided by the proximal section 914 may also function to prevent the can 910 from "popping out" of the distal end of the steering catheter 80 or other overlying delivery member component during deployment of the interventional device. Maintaining the can 910 within the overlying components of the delivery member 70 allows all of the concentric components of the delivery member 70 to be appropriately collapsed when desired and thereby makes retraction of the delivery member 70 out of the heart and the patient's body easier.

A key feature may also be included to maintain rotational alignment of the can 910 with an outer member (e.g., the steering catheter 80 and/or outer sheath 82). The key feature is configured to prevent the can 910 from rotating relative to the outer member even when the can 910 is translated within the outer member. This beneficially aligns preferred bending features (as defined by cut patterns) of the outer member with the bending features of the can 910. The key feature may be formed, for example, as a key on the can 910 and a corresponding keyway groove on the inner surface of the outer member, or vice versa.

The can 910 may be formed from any material suitable for use in an intravascular procedure, including biocompatible polymers and metals. In a preferred embodiment, the can 910 is formed of a material that is substantially similar to a corresponding interventional device intended to be housed within the can. For example, because the can is brought into intimate contact with the interventional device during delivery, it is beneficial to avoid using dissimilar metals which may promote galvanic corrosion of the device or the can. Preferred interventional devices are formed from titanium or a titanium alloy (e.g., nitinol). The can 910 is therefore preferably also formed from titanium or a titanium alloy.

Coil Component for Suture Catheter

As discussed above, it is beneficial for the various component layers of the delivery member 70 to be able to move relative to one another under various challenging curvatures to which the delivery member 70 is subjected during a transseptal approach. Accordingly, it is beneficial for the guidewire tube 86 to be able to translate freely within the suture catheter 72.

The guidewire tube 86 may include a braided polyamide tubing (or other suitable flexible tubing material), and may be sized to be compatible with standard guidewire sizes. For example, the guidewire tube 86 may have an inner diameter of about 0.037 inches so as to be compatible with a standard 0.035 inches guidewire, though other sizes may be utilized according to particular application needs. The wall of the guidewire tube 86 will typically be relatively thin (e.g., about 0.003 to 0.008 inches) to provide effective flexibility to the guidewire tuber 86.

Providing a smooth inner surface within the suture catheter 72, however, can be challenging. In particular, in preferred embodiments where the suture catheter 72 comprises a laser cut hypotube, it can be challenging to achieve a smooth inner surface. For example, the laser cut structure may be too small/tight to allow sufficient electro-polishing. Honing is another option but the length of the laser cut portion of the suture catheter 72 also makes honing very challenging. Other technologies, such as honing and extrude honing, may not produce the desired smoothness of the inner diameter.

Figure 21:
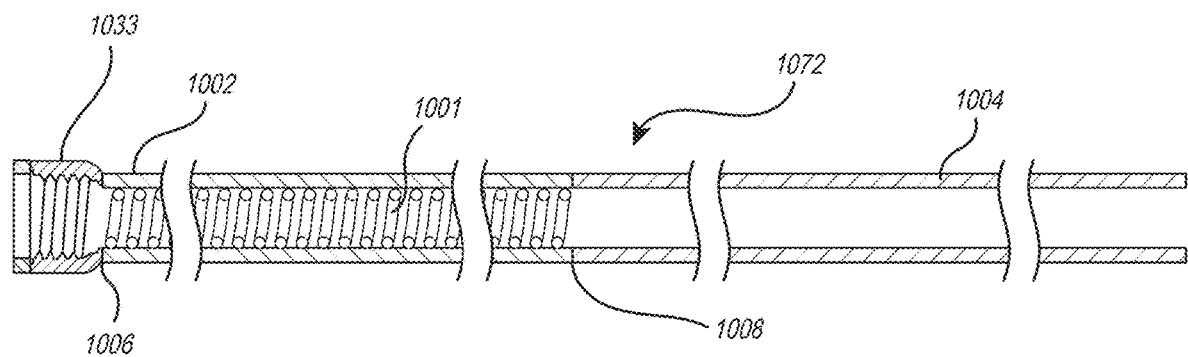
FIG. 21 illustrates an embodiment of a suture catheter including an interior coil component for providing a smooth inner surface to allow other components to freely move within the suture catheter.

FIG. 21 illustrates an alternative embodiment of a suture catheter 1072 that may be utilized, for example, in place of the suture catheter 72 described above. The illustrated suture catheter 1072 includes a coil component 1001 disposed within its inner lumen at least at the distal section 1002 of the inner lumen. The coil component 1001 may be a round wire coil to provide a smooth overall inner surface that resists catching or binding with the guidewire tube 86 when the guidewire tube 86 is inserted therein.

The coil component 1001 may also be stretched somewhat (e.g., 10% to 40% elongation, or 15% to 30% elongation, or about 20% elongation) before it is attached to the inner lumen wall so that it is not in a stacked position and instead allows for bending in various directions before the coils stack against each other.

The coil component 1001 is preferably formed from a material similar to the material forming the wall of the suture catheter 1072, such as stainless steel (e.g., 304 stainless steel). This allows for effective coupling of the coil component 1001 to the inner lumen wall, such as via welding.

In one method of forming the illustrated suture catheter 1072, a distal end of the coil component 1001 is laser welded to the inner lumen surface at or near the distal end 1006 of the distal section 1002 of the suture catheter 1072, the coil is then stretched by a predetermined amount, and the proximal end of the coil component 1001 is then laser welded to the inner lumen surface at a proximal end 1008 of the hypotube making up the distal section 1002 of the suture catheter 1072. A less flexible (e.g., uncut) hypotube portion forming the proximal section 1004 may then be laser welded to the portion making up the distal section 1002. A coating and/or shrink tubing (e.g., PTFE shrink tubing) may also be added to the outer surface of the suture catheter 1072 to aid in movement of the suture catheter 1072 within the delivery catheter 78.

A suture catheter tip ring 1033 may also be laser welded to the distal end 1006 of the distal section 1002. As shown, the suture catheter tip ring 1033 may be threaded so as to receive a connecting structure, such as connecting ring 34, that engages with an interventional device to be delivered by the system.

The coil component 1001 is sized to allow sufficient clearance to receive the guidewire tube 86 when it is inserted therein. In one embodiment, the wires of the coil component 1001 have a diameter of about 0.003 to 0.010 inches, or about 0.004 to 0.008 inches, which may provide a typical clearance of about 0.002 to 0.020 inches.

FURTHER EXEMPLARY EMBODIMENTS

Some additional embodiments are described below by way of example:

Embodiment 1

A delivery system for delivering an interventional device to a targeted anatomical site, the delivery system comprising: an elongated delivery member having a proximal end and a distal end configured for housing the interventional device, and including a plurality of coaxially positioned delivery member components, the plurality of delivery member components including a delivery catheter, an inner catheter coaxially positioned within the delivery catheter and being adapted to maintain a connection with the interventional device until deployment of the interventional device, and a handle assembly for controlling movement of the delivery catheter and inner catheter, the handle assembly including a delivery catheter holder to which a proximal end of the delivery catheter is attached, an inner catheter holder to which a proximal end of the inner catheter is attached, the inner catheter holder being disposed proximal of the delivery catheter holder, and a mechanical linkage that fixes the relative positions of the delivery catheter holder and the inner catheter holder to enable the delivery catheter and the inner catheter to translate together relative to one or more other components of the delivery member, wherein the inner catheter holder includes a quick-release mechanism configured to enable selective decoupling of the inner catheter holder from the mechanical linkage to enable the inner catheter holder to move relative to the delivery catheter holder.

Embodiment 2

The delivery system of Embodiment 1, further comprising one or more alignment rods that extend between the delivery catheter holder and the inner catheter holder, the inner catheter holder being slidable upon the one or more alignment rods when decoupled from the mechanical linkage.

Embodiment 3

The delivery system of Embodiment 1 or Embodiment 2, wherein the inner catheter holder is a cylindrical puck.

Embodiment 4

The delivery system of any one of Embodiments 1 through 3, wherein the inner catheter is a suture catheter having one or more sutures at its distal end for connecting to the interventional device.

Embodiment 5

The delivery system of any one of Embodiments 1 through 4, wherein the inner catheter enters into the delivery catheter at the proximal end of the delivery catheter at the delivery catheter holder.

Embodiment 6

The delivery system of any one of Embodiments 1 through 5, wherein the mechanical linkage comprises a lead rod extending between the delivery catheter holder and the inner catheter holder.

Embodiment 7

The delivery system of any one of Embodiments 1 through 6, wherein the lead rod includes one or more of threads, grooves, and/or depressions which enable engagement with the release mechanism of the inner catheter holder.

Embodiment 8

The delivery system of any one of Embodiments 1 through 7, wherein the release mechanism comprises a pin biased toward a locked position by a spring.

Embodiment 9

The delivery system of any one of Embodiments 1 through 8, wherein the release mechanism further comprises a depressable cap configured such that when depressed, enables the pin to decouple from the mechanical linkage.

Embodiment 10

The delivery system of any one of Embodiments 1 through 9, further comprising a safety mechanism positioned to prevent inadvertent actuation of the release mechanism.

Embodiment 11

The delivery system of any one of Embodiments 1 through 10, wherein the safety mechanism is a safety pin that extends through the release mechanism and prevents depression of the release mechanism unless removed.

Embodiment 12

The delivery system of any one of Embodiments 1 through 11, further comprising a guidewire tube coaxially positioned within the inner catheter, and further comprising a guidewire tube holder to which a proximal end of the guidewire tube is attached, the guidewire tube holder being disposed proximal of the inner catheter holder.

Embodiment 13

The delivery system of any one of Embodiments 1 through 12, wherein the guidewire tube holder is also coupled by the mechanical linkage so as to be positionally fixed relative to the delivery catheter holder.

Embodiment 14

The delivery system of any one of Embodiments 1 through 13, wherein the guidewire tube holder also comprises a quick-release mechanism configured to enable selective decoupling of the guidewire tube holder from the mechanical linkage to enable the guidewire tube holder to move relative to the delivery catheter holder.

Embodiment 15

The delivery system of any one of Embodiments 1 through 14, further comprising: an interventional device formed from nitinol; and an elongated delivery member having a proximal end, a distal end, and an outer sheath, the outer sheath forming an interventional device cover configured to house the interventional device and maintain the interventional device in a compressed, pre-deployed state, the outer sheath being longitudinally translatable relative to the interventional device, wherein at least a portion of the interventional device is biased against an inner surface of the cover when housed within the cover, and wherein the interventional device cover is formed from titanium and wherein the inner surface of the cover is resistant to scratching from the interventional device caused by longitudinal translation of the outer sheath relative to the interventional device.

Embodiment 16

A delivery system for delivering an interventional device to a targeted anatomical site, the delivery system comprising: an interventional device formed from nitinol; and an elongated delivery member having a proximal end, a distal end, and an outer sheath, the outer sheath forming an interventional device cover configured to house the interventional device and maintain the interventional device in a compressed, pre-deployed state, the outer sheath being longitudinally translatable relative to the interventional device, wherein at least a portion of the interventional device is biased against an inner surface of the cover when housed within the cover, and wherein the interventional device cover is formed from titanium and wherein the inner surface of the cover is resistant to scratching from the interventional device caused by longitudinal translation of the outer sheath relative to the interventional device.

Embodiment 17

The delivery system of Embodiment 15 or 16, wherein the cover has a wall thickness of about 0.2 mm to about 0.5 mm, or about 0.3 mm to about 0.4 mm.

Embodiment 18

The delivery system of any one of Embodiments 15 through 17, wherein the cover is sufficiently echotransparent to enable echocardiographic visualization of the interventional device while the device is housed within the cover.

Embodiment 19

The delivery system of any one of Embodiments 15 through 18, wherein the interventional device is a replacement heart valve.

Embodiment 20

The delivery system of any one of Embodiments 15 through 19, wherein the cover further includes a plurality of cuts forming a cut pattern that allows bending of the cover in a single plane.

Embodiment 21

The delivery system of Embodiment 20, wherein the cut pattern enables the cover to bend with a deflection of at least about 75°.

Embodiment 22

The delivery system of any one of Embodiments 15 through 21, wherein a proximal end of the cover is welded to the distal end of the delivery member.

Embodiment 23

The delivery system of any one of Embodiments 15 through 22, wherein a proximal end of the cover is connected to the distal end of the delivery member by a mechanical connection, such as a threaded connection.

Embodiment 24

The delivery system of any one of Embodiments 1 through 23, the delivery system including a steering catheter and the steering catheter comprising: a laser cut hypotube having a proximal end, a distal end, and an inner diameter and an outer diameter at its distal end; and a tip ring having a proximal end and a distal end, the tip ring having a step formed within the interior of its proximal end with a first inner diameter at its proximal end that is slightly larger than the outer diameter of the hypotube, the tip ring having a second inner diameter at its distal end that substantially equal to the inner diameter of the hypotube, wherein the step provides a substantially smooth transition between the inner diameter of the hypotube and the second inner diameter of the tip ring.

Embodiment 25

A delivery system for delivering an interventional device to a targeted anatomical site, the delivery system having a steering catheter and the steering catheter comprising: a laser cut hypotube having a proximal end, a distal end, and an inner diameter and an outer diameter at its distal end; and a tip ring having a proximal end and a distal end, the tip ring having a step formed within the interior of its proximal end with a first inner diameter at its proximal end that is slightly larger than the outer diameter of the hypotube, the tip ring having a second inner diameter at its distal end that substantially equal to the inner diameter of the hypotube, wherein the step provides a substantially smooth transition between the inner diameter of the hypotube and the second inner diameter of the tip ring.

Embodiment 26

The delivery system of Embodiment 24 or Embodiment 25, wherein the tip ring has a substantially rounded distal edge surface at its distal end.

Embodiment 27

The delivery system of any one of Embodiments 24 through 26, wherein the tip ring further comprises a laser-welded seam formed at an interface between the distal end of the hypotube and a distal end of the step of the tip ring.

Embodiment 28

The delivery system of any one of Embodiments 24 through 27, wherein the tip ring further comprises a plurality of lumens through which corresponding tension cables are routed.

Embodiment 29

The delivery system of Embodiment 28, wherein the tip ring further comprises one or more seats each configured to provide a guide surface for routing a corresponding tension cable around and back proximally away from the tip ring.

Embodiment 30

The delivery system of any one of Embodiments 1 through 29, further comprising: a steering catheter having a proximal end, a distal end, and a cut pattern disposed along at least a portion of the steering catheter and that defines a preferred bending direction, wherein the cut pattern includes a series of island cuts aligned on a first side of the steering catheter and a series of corresponding slits on a second, opposite side of the steering catheter that enable the steering catheter to preferentially bend toward the first side and away from the second side, and wherein the cut pattern is arranged such that the island cuts become progressively smaller toward the distal end of the steering catheter.

Embodiment 31

A delivery system for delivering an interventional device to a targeted anatomical site, the delivery system comprising: a steering catheter having a proximal end, a distal end, and a cut pattern disposed along at least a portion of the steering catheter and that defines a preferred bending direction, wherein the cut pattern includes a series of island cuts aligned on a first side of the steering catheter and a series of corresponding slits on a second, opposite side of the steering catheter that enable the steering catheter to preferentially bend toward the first side and away from the second side, and wherein the cut pattern is arranged such that the island cuts become progressively smaller toward the distal end of the steering catheter.

Embodiment 32

The delivery system of Embodiment 30 or Embodiment 31, wherein a distal-most section of the steering catheter omits cuts and thereby forms a straight section.

Embodiment 33

The delivery system of any one of Embodiments 30 through 32, wherein the island cuts form triangle-shaped cutouts.

Embodiment 34

The delivery system of any one of Embodiments 1 through 33, further comprising: outer member; and a delivery catheter disposed within the outer member and longitudinally translatable within the outer member, the delivery catheter having a proximal section and a distal section, wherein at least the distal section of the delivery catheter includes a coil section and a braid section surrounding the coil section and attached thereto.

Embodiment 35

A delivery system for delivering an interventional device to a targeted anatomical site, the delivery system comprising: an outer member; and a delivery catheter disposed within the outer member and longitudinally translatable within the outer member, the delivery catheter having a proximal section and a distal section, wherein at least the distal section of the delivery catheter includes a coil section and a braid section surrounding the coil section and attached thereto.

Embodiment 36

The delivery system of Embodiment 34 or Embodiment 35, wherein the braid section is attached to the coil section with sufficient slack to allow the distal section of the delivery catheter to bend about 0° to about 180°, about 180° to about 540°, or about 270° to about 360°.

Embodiment 37

The delivery system of any one of Embodiments 34 through 36, wherein the proximal section is a hypotube.

Embodiment 38

The delivery system of any one of Embodiments 34 through 37, further comprising a spacer ring disposed between the distal section and proximal section, the spacer ring being joined to the coil section of the distal section and to an outer surface of the proximal section.

Embodiment 39

The delivery system of any one of Embodiments 1 through 38, further comprising: an elongated delivery member coupled to a handle assembly and extending distally from the handle assembly, the delivery member including an outer member; and a delivery catheter concentrically disposed within the outer member, the delivery member having a can structure disposed at a distal end, the can structure being configured to at least partially house an interventional device radially within the can structure and to maintain the interventional device in a compressed, pre-deployed state, wherein at least a portion of the can structure includes a cut pattern providing preferential bending of the can structure along at least one plane.

Embodiment 40

A delivery system for delivering an interventional device to a targeted anatomical site, the delivery system comprising: an elongated delivery member coupled to a handle assembly and extending distally from the handle assembly, the delivery member including an outer member; and a delivery catheter concentrically disposed within the outer member, the delivery member having a can structure disposed at a distal end, the can structure being configured to at least partially house an interventional device radially within the can structure and to maintain the interventional device in a compressed, pre-deployed state, wherein at least a portion of the can structure includes a cut pattern providing preferential bending of the can structure along at least one plane.

Embodiment 41

The delivery system of Embodiment 39 or Embodiment 40, wherein the outer member includes a steering catheter configured to curve the delivery member in a compound curve that enables intravascular delivery of the delivery member to a targeted cardiac valve.

Embodiment 42

The delivery system of any one of Embodiments 39 through 41, wherein the delivery catheter is axially translatable relative to the outer member.

Embodiment 43

The delivery system of any one of Embodiments 39 through 42, wherein the interventional device is positioned within the can structure such that a proximal portion of the interventional device is housed within the can structure and a distal portion of the interventional device extends distally out of the can structure.

Embodiment 44

The delivery system of any one of Embodiments 39 through 43, wherein the can structure includes a proximal section and a distal section separated by a divider.

Embodiment 45

The delivery system of Embodiment 44, wherein only the proximal section includes the cut pattern.

Embodiment 46

The delivery system of Embodiment 44 or Embodiment 45, wherein the delivery catheter extends through the proximal section of the can structure and couples to the can structure at the divider.

Embodiment 47

The delivery system of any one of Embodiments 39 through 46, wherein the outer member includes a cut pattern that provides preferred bending in at least one preferred plane, and wherein the cut pattern of the can structure provides preferred bending of the can structure in substantially the same preferred plane.

Embodiment 48

The delivery system of any one of Embodiments 39 through 47, wherein the outer member and the can structure include a key feature configured to rotationally align the can structure to the outer member.

Embodiment 49

The delivery system of any one of Embodiments 39 through 48, wherein the can structure is formed of titanium or a titanium alloy.

Embodiment 50

A method of deploying an interventional device at a targeted cardiac valve, the method comprising: providing a delivery system as in any one of Embodiments 1 through 49; routing the delivery member of the delivery system through a patient's vasculature such that the interventional device located at the distal end of the delivery member is positioned at the targeted cardiac valve; partially deploying the interventional device on a first side of the targeted cardiac valve; actuating the quick-release mechanism of the inner catheter holder; and moving the inner catheter holder relative to the delivery catheter holder to cause the inner catheter to move relative to the delivery catheter and thereby further deploy the interventional device.

Embodiment 51

The method of Embodiment 50, wherein the targeted cardiac valve is a mitral valve, and wherein the mitral valve is approached via a transseptal approach.

CONCLUSION

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. A delivery system for delivering an interventional device to a targeted anatomical site, the delivery system comprising:
    an elongated delivery member having a proximal end and a distal end configured for housing the interventional device, and including a plurality of coaxially positioned delivery member components, the plurality of delivery member components including:
        a delivery catheter,
        an inner catheter coaxially positioned within the delivery catheter and adapted to maintain a connection with the interventional device until deployment of the interventional device; and
    a handle assembly for controlling movement of the delivery catheter and the inner catheter, the handle assembly including:
        a delivery catheter holder to which a proximal end of the delivery catheter is attached;
        an inner catheter holder to which a proximal end of the inner catheter is attached, the inner catheter holder being disposed proximal of the delivery catheter holder;
        a mechanical linkage that fixes the relative positions of the delivery catheter holder and the inner catheter holder to enable the delivery catheter and the inner catheter to translate together relative to one or more other components of the delivery member; and
    a steering catheter, the steering catheter comprising:
        a laser cut hypotube having a proximal end, a distal end, and an inner diameter and an outer diameter at its distal end; and
        a tip ring having a proximal end and a distal end, the tip ring having a step formed within an interior of its proximal end with a first inner diameter at its proximal end that is slightly larger than the outer diameter of the hypotube, the tip ring having a second inner diameter at its distal end that is substantially equal to the inner diameter of the hypotube,
        wherein the step provides a substantially smooth transition between the inner diameter of the hypotube and the second inner diameter of the tip ring,
    wherein the inner catheter holder includes a quick-release mechanism configured to enable selective decoupling of the inner catheter holder from the mechanical linkage to enable the inner catheter holder to move relative to the delivery catheter holder.

2. The delivery system of claim 1, further comprising an interventional device formed from nitinol configured to be housed within an outer sheath of the elongated delivery member,
    wherein the outer sheath forms an interventional device cover configured to house the interventional device and maintain the interventional device in a compressed, pre-deployed state, the outer sheath being longitudinally translatable relative to the interventional device,
    wherein at least a portion of the interventional device is biased against an inner surface of the cover when housed within the cover, and
    wherein the interventional device cover is formed from titanium and wherein the inner surface of the cover is resistant to scratching from the interventional device caused by longitudinal translation of the outer sheath relative to the interventional device.

3. The delivery system of claim 2, wherein the cover further includes a plurality of cuts forming a cut pattern that allows bending of the cover in a single plane, wherein the cut pattern enables the cover to bend with a deflection of at least about 75°.

4. The delivery system of claim 2, wherein a proximal end of the cover is connected to the distal end of the delivery member by a mechanical connection a threaded connection.

5. The delivery system of claim 1, wherein the elongated delivery member further comprises a steering catheter, the steering catheter having cut pattern disposed along at least a portion of the steering catheter and that defines a preferred bending direction,
    wherein the cut pattern includes a series of island cuts aligned on a first side of the steering catheter and a series of corresponding slits on a second, opposite side of the steering catheter that enable the steering catheter to preferentially bend toward the first side and away from the second side, and
    wherein the cut pattern is arranged such that the island cuts become progressively smaller toward the distal end of the steering catheter.

6. The delivery system of claim 1, wherein at least a distal section of the delivery catheter includes a coil section and a braid section surrounding the coil section and attached thereto.

7. The delivery system of claim 6, wherein the braid section is attached to the coil section with sufficient slack to allow the distal section of the delivery catheter to bend about 180° to about 540°.

8. The delivery system of claim 1, wherein the delivery catheter includes a can structure disposed at a distal end, the can structure being configured to at least partially house an interventional device radially within the can structure and to maintain the interventional device in a compressed, pre-deployed state, wherein at least a portion of the can structure includes a cut pattern providing preferential bending of the can structure along at least one plane.

9. The delivery system of claim 8, wherein the can structure includes a proximal section and a distal section separated by a divider, and wherein only the proximal section includes the cut pattern.

10. The delivery system of claim 9, wherein the delivery catheter extends through the proximal section of the can structure and couples to the can structure at the divider.

11. The delivery system of claim 1, further comprising one or more alignment rods that extend between the delivery catheter holder and the inner catheter holder, the inner catheter holder being slidable upon the one or more alignment rods when decoupled from the mechanical linkage.

12. The delivery system of claim 1, wherein the inner catheter is a suture catheter having one or more sutures at its distal end for connecting to the interventional device.

13. The delivery system of claim 1, wherein the mechanical linkage comprises a lead rod extending between the delivery catheter holder and the inner catheter holder.

14. The delivery system of claim 13, wherein the lead rod includes one or more of threads, grooves, and/or depressions which enable engagement with the release mechanism of the inner catheter holder.

15. A delivery system for delivering an interventional device to a targeted anatomical site, the delivery system comprising:
    an elongated delivery member having a proximal end and a distal end configured for housing the interventional device, and including a plurality of coaxially positioned delivery member components, the plurality of delivery member components including:
        an outer sheath that forms an interventional device cover configured to house the interventional device and maintain the interventional device in a compressed, pre-deployed state, wherein the interventional device cover is formed from titanium and wherein an inner surface of the cover is resistant to scratching from the interventional device caused by longitudinal translation of the outer sheath relative to the interventional device;
        a steering catheter coaxially positioned within the outer sheath, the steering catheter having a cut pattern disposed along at least a portion of the steering catheter that defines a preferred bending direction, wherein the cut pattern includes a series of island cuts aligned on a first side of the steering catheter and arranged to become progressively smaller toward a distal end and a series of corresponding slits on a second, opposite side of the steering catheter that enable the steering catheter to preferentially bend toward the first side and away from the second side;
        a delivery catheter coaxially positioned within the steering catheter, wherein at least a distal section of the delivery catheter includes a coil section and a braid section surrounding the coil section and attached thereto; and
        an inner catheter coaxially positioned within the delivery catheter and adapted to maintain a connection with the interventional device until deployment of the interventional device; and
    a handle assembly for controlling movement of the delivery catheter and inner catheter, the handle assembly including:
        a delivery catheter holder to which a proximal end of the delivery catheter is attached;
        an inner catheter holder to which a proximal end of the inner catheter is attached, the inner catheter holder being disposed proximal of the delivery catheter holder; and
        a mechanical linkage that fixes the relative positions of the delivery catheter holder and the inner catheter holder to enable the delivery catheter and the inner catheter to translate together relative to one or more other components of the delivery member;
    wherein the inner catheter holder includes a quick-release mechanism configured to enable selective decoupling of the inner catheter holder from the mechanical linkage to enable the inner catheter holder to move relative to the delivery catheter holder.

16. The delivery system of claim 15, wherein the steering catheter further comprises a laser cut hypotube having a proximal end, a distal end, and an inner diameter and an outer diameter at its distal end, and a tip ring having a proximal end and a distal end, the tip ring having a step formed within an interior of its proximal end with a first inner diameter at its proximal end that is slightly larger than the outer diameter of the hypotube, the tip ring having a second inner diameter at its distal end that substantially equal to the inner diameter of the hypotube.

17. The delivery system of claim 15, wherein the delivery catheter includes a can structure disposed at a distal end, the can structure being configured to at least partially house an interventional device radially within the can structure and to maintain the interventional device in a compressed, pre-deployed state, wherein at least a portion of the can structure includes a cut pattern providing preferential bending of the can structure along at least one plane.

18. An elongated delivery member for delivering an interventional device to a targeted anatomical site, the elongated delivery member comprising:
    a proximal end and a distal end configured for housing the interventional device; and
    a plurality of coaxially positioned delivery member components, the plurality of delivery member components including:
        an outer sheath that forms an interventional device cover configured to house the interventional device and maintain the interventional device in a compressed, pre-deployed state, wherein the interventional device cover is formed from titanium and wherein an inner surface of the cover is resistant to scratching from the interventional device caused by longitudinal translation of the outer sheath relative to the interventional device;
        a steering catheter coaxially positioned within the outer sheath;
        a delivery catheter coaxially positioned within the steering catheter, wherein at least a distal section of the delivery catheter includes a coil section and a braid section surrounding the coil section and attached thereto, and wherein the delivery catheter includes a can structure disposed at a distal end, the can structure being configured to at least partially house the interventional device radially within the can structure and to maintain the interventional device in a compressed, pre-deployed state, wherein at least a portion of the can structure includes a cut pattern providing preferential bending of the can structure along at least one plane; and an inner catheter coaxially positioned within the delivery catheter and being adapted to maintain a connection with the interventional device until deployment of the interventional device.

19. The delivery member of claim 18, wherein the steering catheter includes a cut pattern disposed along at least a portion of the steering catheter that defines a preferred bending direction, wherein the cut pattern includes a series of island cuts aligned on a first side of the steering catheter and arranged to become progressively smaller toward a distal end and a series of corresponding slits on a second, opposite side of the steering catheter that enable the steering catheter to preferentially bend toward the first side and away from the second side.

* * * * *